(12) United States Patent
Vaidya et al.

(10) Patent No.: US 12,266,107 B1
(45) Date of Patent: Apr. 1, 2025

(54) SYSTEM AND METHOD FOR RESPONDING TO A USER INPUT USING AN AGENT ORCHESTRATOR

(71) Applicant: Anumana, Inc., Cambridge, MA (US)

(72) Inventors: Suthirth Vaidya, Bengaluru (IN); Rakesh Barve, Bengaluru (IN); Abhijith Chunduru, Bengaluru (IN); Murali Aravamudan, Andover, MA (US); Animesh Agarwal, San Mateo, CA (US); Samir Awasthi, Boston, MA (US); Maulik Nanavaty, Cambridge, MA (US); Sai Saketh Chennamsetty, Bengaluru (IN); Arjun Puranik, San Jose, CA (US); Harish Kumar B V, Salem (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/810,128

(22) Filed: Aug. 20, 2024

(51) Int. Cl.
*G06T 7/00* (2017.01)
*G16H 10/60* (2018.01)

(52) U.S. Cl.
CPC .......... *G06T 7/0012* (2013.01); *G16H 10/60* (2018.01); *G06T 2207/10136* (2013.01); *G06T 2207/20081* (2013.01)

(58) Field of Classification Search
None
See application file for complete search history.

(56) References Cited

U.S. PATENT DOCUMENTS

| | | | |
|---|---|---|---|
| 11,564,591 B1* | 1/2023 | Narayan | G16H 40/63 |
| 2017/0103532 A1* | 4/2017 | Ghesu | A61B 5/7264 |
| 2017/0116497 A1* | 4/2017 | Georgescu | G06N 3/006 |
| 2021/0334067 A1 | 10/2021 | Thakkar | |
| 2021/0391082 A1* | 12/2021 | Amos | G06N 3/044 |
| 2022/0005198 A1* | 1/2022 | Goldberg | A61B 5/364 |
| 2022/0248956 A1* | 8/2022 | Haeusser | A61B 5/742 |
| 2022/0391729 A1* | 12/2022 | Duford | G06Q 10/0633 |
| 2023/0165638 A1* | 6/2023 | Mansi | A61B 34/10 604/500 |

(Continued)

FOREIGN PATENT DOCUMENTS

| | | |
|---|---|---|
| WO | 2019094090 A1 | 5/2019 |
| WO | 2023196607 A1 | 10/2023 |

*Primary Examiner* — Nancy Bitar
(74) *Attorney, Agent, or Firm* — Caldwell Intellectual Property Law

(57) ABSTRACT

Described herein are systems and methods for responding to user input using an agent orchestrator. A system may include a cardiac catheter, a user interface, and a computing device configured to receive, from the user interface, a first user input, receive, from the catheter, the procedure data, determine, using an agent orchestrator, a first agent selection datum, wherein determining the first agent selection datum includes generating the first agent selection datum as a function of the first user input using a trained agent selection machine learning model, using a first agent corresponding to the first agent selection datum, determine a first agent output, wherein determining the first agent output includes inputting into the first agent the procedure data, and receiving, as an output from the first agent, the first agent output, and display, using the user interface, the first agent output.

16 Claims, 11 Drawing Sheets

(56) References Cited

U.S. PATENT DOCUMENTS

| 2023/0255684 A1* | 8/2023 | Schmidt | A61B 18/1492 |
| | | | 606/41 |
| 2024/0112819 A1* | 4/2024 | Paamand | G16H 20/40 |
| 2024/0189032 A1* | 6/2024 | Zoubi | A61B 18/1492 |

* cited by examiner

SYSTEM AND METHOD FOR RESPONDING TO A USER INPUT USING AN AGENT ORCHESTRATOR

FIELD OF THE INVENTION

The present invention generally relates to the field of machine learning. In particular, the present invention is directed to a system and method for responding to a user input using an agent orchestrator.

BACKGROUND

Electrophysiology (EP) procedures are complex and require precise and continuous monitoring. Traditional methods rely heavily on manual processes and the expertise of the physician. This can lead to variability in outcomes.

SUMMARY OF THE DISCLOSURE

In an aspect, described herein are systems and methods for responding to user input using an agent orchestrator. A system may include a cardiac catheter, a user interface, at least a processor, and a memory communicatively connected to the at least a processor, wherein the memory contains instructions configuring the at least a processor to receive, from the user interface, a first user input, receive, from the catheter, the procedure data, determine, using an agent orchestrator, a first agent selection datum, wherein determining the first agent selection datum includes generating the first agent selection datum as a function of the first user input using a trained agent selection machine learning model, using a first agent corresponding to the first agent selection datum, determine a first agent output, wherein determining the first agent output includes inputting into the first agent the procedure data, and receiving, as an output from the first agent, the first agent output, and display, using the user interface, the first agent output.

In another aspect, described herein is a method of responding to a user input using an agent orchestrator. Such a method may include, using at least a processor, receiving, from a user interface, a first user input, using the at least a processor, receiving, from a catheter, procedure data, using the at least a processor and an agent orchestrator, determining a first agent selection datum, wherein determining the first agent selection datum includes generating the first agent selection datum as a function of the first user input using a trained agent selection machine learning model, using the at least a processor and a first agent corresponding to the first agent selection datum, determining a first agent output, wherein determining the first agent output includes inputting into the first agent the procedure data, and receiving, as an output from the first agent, the first agent output, and using the at least a processor and the user interface, displaying the first agent output.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for responding to a user input using an agent orchestrator. A system may receive, from a user interface, a user input such as text or speech. A system may, using an agent orchestrator, select an appropriate agent. Such agent may receive additional data, such as procedure data or electronic health record data, as an input, and may produce an output which is responsive to the user input.

Figure 1:
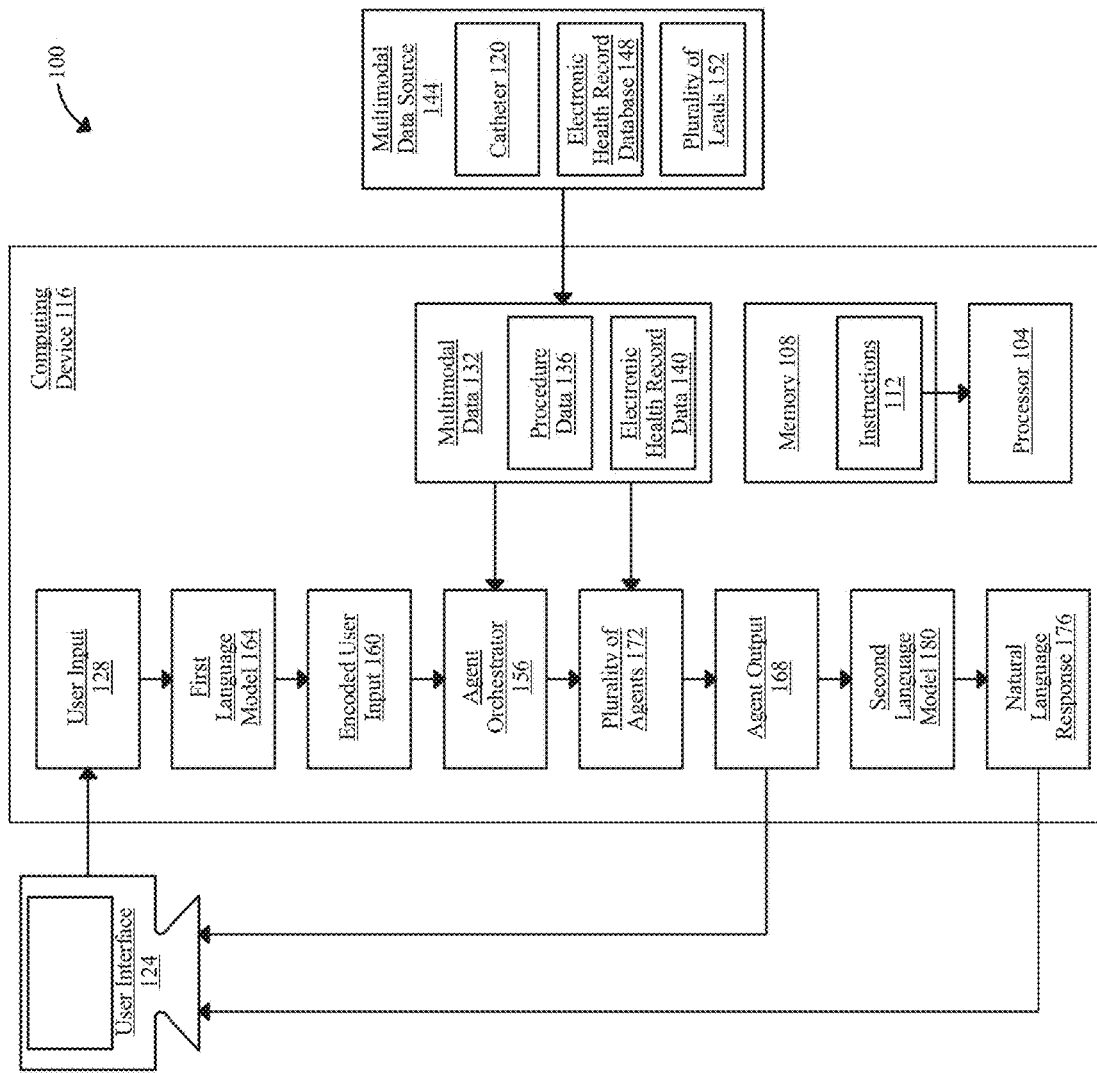
FIG. 1 is a diagram depicting an exemplary embodiment of a system for responding to a user input using an agent orchestrator.

Referring now to FIG. 1, an exemplary embodiment of a system 100 for responding to a user input using an agent orchestrator is illustrated. System 100 may include a computing device. System 100 may include a processor. Processor may include, without limitation, any processor described in this disclosure. Processor may be included in computing device. Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device.

Still referring to FIG. 1, in some embodiments, system 100 may include at least a processor 104 and a memory 108 communicatively connected to the at least a processor 104, the memory 108 containing instructions 112 configuring the at least a processor 104 to perform one or more processes described herein. Computing device 116 may include processor 104 and/or memory 108. Computing device 116 may be configured to perform one or more processes described herein.

Still referring to FIG. 1, computing device 116 may include but is not limited to, for example, a computing device or cluster of computing devices in a first location and a second computing device or cluster of computing devices in a second location. Computing device 116 may include one or more computing devices dedicated to data storage, security, distribution of traffic for load balancing, and the like. Computing device 116 may distribute one or more computing tasks as described below across a plurality of computing devices of computing device, which may operate in parallel, in series, redundantly, or in any other manner used for distribution of tasks or memory between computing devices. Computing device 116 may be implemented, as a non-limiting example, using a "shared nothing" architecture.

Still referring to FIG. 1, computing device 116 may be designed and/or configured to perform any method, method step, or sequence of method steps in any embodiment described in this disclosure, in any order and with any degree of repetition. For instance, computing device 116 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 116 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, as used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, in some embodiments, system 100 may include a catheter 120. As used herein, a "catheter" is a medical device comprising a tube which may be inserted into a passageway of a subject. In some embodiments, catheter 120 may include a cardiac catheter. As used herein, a "cardiac catheter" is a catheter configured for use in the heart. Catheter 120 may be used to, in non-limiting examples, examine and/or replace heart valves, repair heart defects, take samples of blood and/or heart muscle, inject dye into arteries, and/or capture an ultrasonic image. In some embodiments, catheter 120 and/or a process using catheter 120, such as capturing and/or processing an ultrasonic image, may be consistent with U.S. patent application Ser. No. 18/395,087, filed on Dec. 22, 2023, and titled "APPARATUS AND METHOD FOR GENERATING A THREE-DIMENSIONAL (3D) MODEL OF CARDIAC ANATOMY WITH AN OVERLAY," the entirety of which is hereby incorporated by reference.

Still referring to FIG. 1, in some embodiments, system 100 may include user interface 124. User interface 124 may include, in non-limiting examples, a smartphone, smartwatch, laptop computer, desktop computer, virtual reality device, tablet, and/or a component thereof. User interface 124 may include an input interface and/or an output interface. An input interface may include one or more mechanisms for a computing device to receive data from a user such as, in non-limiting examples, a mouse, keyboard, button, scroll wheel, camera, microphone, switch, lever, touchscreen, trackpad, joystick, and controller. An output interface may include one or more mechanisms for a computing device to output data to a user such as, in non-limiting examples, a screen, speaker, and haptic feedback system. An output interface may be used to display one or more elements of data described herein. As used herein, a device "displays" a datum if the device outputs the datum in a format suitable for communication to a user. For example, a device may display a datum by outputting text or an image on a screen or outputting a sound using a speaker.

Still referring to FIG. 1, in some embodiments, system 100 may receive, using user interface 124, a user input 128. As used herein, a "user interface" is a mechanism by which a user may input information into a computing device, a mechanism by which a computing device may output information to a user, or both. As used herein, a "user input" is a datum generated as a function of an interaction between a user and an input interface. A user input may include, in non-limiting examples, a request by a user for a particular datum and/or another prompt input by a user. In a non-limiting example, a user input may include a request that system 100 display a particular electronic health record of a subject. In another non-limiting example, a user input may include a question as to whether a user's electrocardiogram (ECG) data suggests that a user has a particular cardiac condition. In some embodiments, user input 128 may include text input data. In some embodiments, user input 128 may include audio input data. As used herein, "audio input data" is data representing sound recorded by a sensor. Audio input data may include, in a non-limiting example, a spoken prompt by a user which is captured using a microphone.

Still referring to FIG. 1, in some embodiments, audio input data may be processed using automatic speech recognition. For example, audio input data may be transcribed using an automatic speech recognition process. In some embodiments, automatic speech recognition may require training (i.e., enrollment). In some cases, training an automatic speech recognition model may require an individual speaker to read text or isolated vocabulary. In some cases, audio training data may include an audio component having an audible verbal content, the contents of which are known a priori by a computing device. Computing device may then train an automatic speech recognition model according to training data which includes audible verbal content correlated to known content. In this way, computing device may analyze a person's specific voice and train an automatic speech recognition model to the person's speech, resulting in increased accuracy. Alternatively, or additionally, in some cases, computing device may include an automatic speech recognition model that is speaker independent. As used in this disclosure, a "speaker independent" automatic speech recognition process is an automatic speech recognition process that does not require training for each individual speaker. Conversely, as used in this disclosure, automatic speech recognition processes that employ individual speaker specific training are "speaker dependent"

Still referring to FIG. 1, in some embodiments, an automatic speech recognition process may perform voice recognition or speaker identification. As used in this disclosure, "voice recognition" is a process of identifying a speaker, from audio content, rather than what the speaker is saying. In some cases, computing device may first recognize a speaker of verbal audio content and then automatically recognize speech of the speaker, for example by way of a speaker dependent automatic speech recognition model or process. In some embodiments, an automatic speech recognition process can be used to authenticate or verify an identity of a speaker. In some cases, a speaker may or may not include subject. For example, subject may speak within audio input data, but others may speak as well.

Still referring to FIG. 1, in some embodiments, an automatic speech recognition process may include one or all of acoustic modeling, language modeling, and statistically based speech recognition algorithms. In some cases, an automatic speech recognition process may employ hidden Markov models (HMMs). As discussed in greater detail below, language modeling such as that employed in natural language processing applications like document classification or statistical machine translation, may also be employed by an automatic speech recognition process.

Still referring to FIG. 1, an exemplary algorithm employed in automatic speech recognition may include or even be based upon hidden Markov models. Hidden Markov models (HMMs) may include statistical models that output a sequence of symbols or quantities. HMMs can be used in speech recognition because a speech signal can be viewed as a piecewise stationary signal or a short-time stationary signal. For example, over a short time scale (e.g., 10 milliseconds), speech can be approximated as a stationary process. Speech (i.e., audible verbal content) can be understood as a Markov model for many stochastic purposes.

Still referring to FIG. 1, in some embodiments HMMs can be trained automatically and may be relatively simple and computationally feasible to use. In an exemplary automatic speech recognition process, a hidden Markov model may output a sequence of n-dimensional real-valued vectors (with n being a small integer, such as 10), at a rate of about one vector every 10 milliseconds. Vectors may consist of cepstral coefficients. A cepstral coefficient requires using a spectral domain. Cepstral coefficients may be obtained by taking a Fourier transform of a short time window of speech yielding a spectrum, decorrelating the spectrum using a cosine transform, and taking first (i.e., most significant) coefficients. In some cases, an HMM may have in each state a statistical distribution that is a mixture of diagonal covariance Gaussians, yielding a likelihood for each observed vector. In some cases, each word, or phoneme, may have a different output distribution; an HMM for a sequence of words or phonemes may be made by concatenating an HMMs for separate words and phonemes.

Still referring to FIG. 1, in some embodiments, an automatic speech recognition process may use various combinations of a number of techniques in order to improve results. In some cases, a large-vocabulary automatic speech recognition process may include context dependency for phonemes. For example, in some cases, phonemes with different left and right context may have different realizations as HMM states. In some cases, an automatic speech recognition process may use cepstral normalization to normalize for different speakers and recording conditions. In some cases, an automatic speech recognition process may use vocal tract length normalization (VTLN) for male-female normalization and maximum likelihood linear regression (MLLR) for more general speaker adaptation. In some cases, an automatic speech recognition process may determine so-called delta and delta-delta coefficients to capture speech dynamics and might use heteroscedastic linear discriminant analysis (HLDA). In some cases, an automatic speech recognition process may use splicing and a linear discriminate analysis (LDA)-based projection, which may include heteroscedastic linear discriminant analysis or a global semi-tied covariance transform (also known as maximum likelihood linear transform [MLLT]). In some cases, an automatic speech recognition process may use discriminative training techniques, which may dispense with a purely statistical approach to HMM parameter estimation and instead optimize some classification-related measure of training data; examples may include maximum mutual information (MMI), minimum classification error (MCE), and minimum phone error (MPE).

Still referring to FIG. 1, in some embodiments, an automatic speech recognition process may be said to decode speech (i.e., audible verbal content). Decoding of speech may occur when an automatic speech recognition system is presented with a new utterance and must compute a most likely sentence. In some cases, speech decoding may include a Viterbi algorithm. A Viterbi algorithm may include a dynamic programming algorithm for obtaining a maximum a posteriori probability estimate of a most likely sequence of hidden states (i.e., Viterbi path) that results in a sequence of observed events. Viterbi algorithms may be employed in context of Markov information sources and hidden Markov models. A Viterbi algorithm may be used to find a best path, for example using a dynamically created combination hidden Markov model, having both acoustic and language model information, using a statically created combination hidden Markov model (e.g., finite state transducer [FST] approach).

Still referring to FIG. 1, in some embodiments, speech (i.e., audible verbal content) decoding may include considering a set of good candidates and not only a best candidate, when presented with a new utterance. In some cases, a better scoring function (i.e., re-scoring) may be used to rate each of a set of good candidates, allowing selection of a best candidate according to this refined score. In some cases, a set of candidates can be kept either as a list (i.e., N-best list approach) or as a subset of models (i.e., a lattice). In some cases, re-scoring may be performed by optimizing Bayes risk (or an approximation thereof). In some cases, re-scoring may include optimizing for sentence (including keywords) that minimizes an expectancy of a given loss function with regards to all possible transcriptions. For example, re-scoring may allow selection of a sentence that minimizes an average distance to other possible sentences weighted by their estimated probability. In some cases, an employed loss function may include Levenshtein distance, although different distance calculations may be performed, for instance for specific tasks. In some cases, a set of candidates may be pruned to maintain tractability.

Still referring to FIG. 1, in some embodiments, an automatic speech recognition process may employ dynamic time warping (DTW)-based approaches. Dynamic time warping may include algorithms for measuring similarity between two sequences, which may vary in time or speed. For instance, similarities in walking patterns would be detected, even if in one video the person was walking slowly and if in another he or she were walking more quickly, or even if there were accelerations and deceleration during the course of one observation. DTW has been applied to video, audio, and graphics—indeed, any data that can be turned into a linear representation can be analyzed with DTW. In some cases, DTW may be used by an automatic speech recognition process to cope with different speaking (i.e., audible verbal content) speeds. In some cases, DTW may allow computing device to find an optimal match between two given sequences (e.g., time series) with certain restrictions. That is, in some cases, sequences can be "warped" non-linearly to match each other. In some cases, a DTW-based sequence alignment method may be used in context of hidden Markov models.

Still referring to FIG. 1, in some embodiments, an automatic speech recognition process may include a neural network. Neural network may include any neural network, for example those disclosed with reference to FIGS. 3-5. In some cases, neural networks may be used for automatic speech recognition, including phoneme classification, phoneme classification through multi-objective evolutionary algorithms, isolated word recognition, audiovisual speech recognition, audiovisual speaker recognition and speaker adaptation. In some cases, neural networks employed in automatic speech recognition may make fewer explicit assumptions about feature statistical properties than HMMs and therefore may have several qualities making them attractive recognition models for speech recognition. When used to estimate the probabilities of a speech feature segment, neural networks may allow discriminative training in a natural and efficient manner. In some cases, neural networks may be used to effectively classify audible verbal content over short-time interval, for instance such as individual phonemes and isolated words. In some embodiments, a neural network may be employed by automatic speech recognition processes for pre-processing, feature transformation and/or dimensionality reduction, for example prior to HMM-based recognition. In some embodiments, long short-term memory (LSTM) and related recurrent neural networks (RNNs) and Time Delay Neural Networks (TDNN's) may be used for automatic speech recognition, for example over longer time intervals for continuous speech recognition.

Still referring to FIG. 1, in some embodiments, system 100 may receive data of one or more modalities, such as multimodal data 132. Data received, such as multimodal data 132, may include in non-limiting examples, procedure data 136 and/or electronic health record data 140. Multimodal data 132 and/or a datum thereof may be received from multimodal data source 144 such as catheter 120, electronic health record database 148, and/or plurality of leads 152.

Still referring to FIG. 1, in some embodiments, system 100 may receive procedure data 136. As used herein, "procedure data" is data collected in preparation for a medical procedure, data collected during a medical procedure, data collected as a result of a medical procedure, or a combination thereof, where the data describes the subject, the procedure, or both. In some embodiments, procedure data 136 may include cardiac procedure data. As used herein, "cardiac procedure data" is data collected in preparation for a cardiac procedure, data collected during a cardiac procedure, data collected as a result of a cardiac procedure, or a combination thereof, where the data describes the subject, the cardiac procedure, or both. In some embodiments, catheter 120 may be configured to capture procedure data 136. In some embodiments, procedure data 136 may be received from a sensor of catheter 120. In some embodiments, cardiac procedure data may be received from a sensor of a cardiac catheter. In some embodiments, procedure data 136 may include an ECG datum. In some embodiments, an ECG datum may be received from plurality of leads 152. In some embodiments, an ECG datum and/or methods of generating, receiving, and/or processing an ECG datum may be consistent with U.S. patent application Ser. No. 18/653,425, filed on May 2, 2024, and titled "SYSTEMS AND METHODS FOR SIGNAL DIGITIZATION," the entirety of which is hereby incorporated by reference. In some embodiments, an ECG datum may include historical ECG data of a subject and/or may be retrieved from electronic health record database 148. In some embodiments, procedure data 136 may include catheter location data. As used herein, "catheter location data" is data describing a location of a catheter, data describing a location of a component of a catheter, or both. In some embodiments, catheter location data may include cardiac catheter location data. As used herein, "cardiac catheter location data" is data describing a location of a cardiac catheter, data describing a location of a component of a cardiac catheter, or both. In some embodiments, procedure data 136 may include ultrasonic image data. In some embodiments, procedure data 136 may include a Pulsed Field Ablation (PFA) device parameter. In some embodiments, procedure data 136, methods of processing procedure data 136, and/or methods of gathering procedure data 136 may be consistent with U.S. patent application Ser. No. 18/646,991, filed on Apr. 26, 2024, and titled "METHOD AND APPARATUS FOR PREDICTING PULSED FIELD ABLATION DURABILITY," the entirety of which is hereby incorporated by reference. In a non-limiting example, procedure data 136 may include heart rate data of a subject from a heart rate sensor. Procedure data 136 may include, in additional non-limiting examples, ultrasonic image data, echocardiogram data, intracardiac echo (ICE) image data, transthoracic echocardiogram (TTE) data, transesophageal echocardiogram (TEE) data, and point of care ultrasound (POCUS) data. Procedure data 136 may include, in additional non-limiting examples, data gathered by a catheter configured for ablation, mapping, and/or ICE imaging. In some embodiments, system 100 may include an ultrasound device configured to generate ultrasound data. In some embodiments, system may include an ICE catheter configured to detect ICE data.

Still referring to FIG. 1, in some embodiments, system 100 may receive electronic health record data 140 from electronic health record database 148. As used herein, "electronic health record data" is digital data describing a health state of a subject, digital data describing a historical health state of a subject, digital data describing a historical medical event of a subject, or a combination thereof. Electronic health record data may include, in non-limiting examples, data describing a medical procedure performed on a subject, data describing a symptom of a medical condition of a subject, and results of a medical test performed on a subject.

Still referring to FIG. 1, in some embodiments, system 100 may determine, using agent orchestrator 156, an agent selection datum. As used herein, an "agent orchestrator" is a system for activating one or more agents. As used herein, an "agent selection datum" is a datum identifying an agent to be activated. As used herein, an "agent" is a computer program which acts at the instruction of another computer program. In some embodiments, system 100 may determine an agent selection datum based on a user input. In some embodiments, system 100 may determine an agent selection datum using an agent selection machine learning model. Agent selection machine learning model may be trained using a supervised learning algorithm. Agent selection machine learning model may include a classifier. Agent selection machine learning model may include a neural network. Agent selection machine learning model may be trained on a training dataset including example user inputs, associated with example agent selection data. Such a training dataset may be obtained by, for example, manually assigning prompts to the appropriate agents. In some embodiments, a pre-trained model may be used, such as a pre-trained language model. In some embodiments, a pre-trained model may be fine-tuned to a task of assigning prompts to agents. Once agent selection machine learning model is trained, it may be used to determine an agent selection datum. System 100 may input a user input into agent selection machine learning model, and system 100 may receive an agent selection datum from the model.

Still referring to FIG. 1, in some embodiments, agent selection machine learning model may include a language model. In some embodiments, inputs to agent selection machine learning model may include user input 128. In some embodiments, user input 128 may be transcribed using an automatic speech recognition system as described above before being input into agent selection machine learning model. In some embodiments, a language model may include a large language model. In some embodiments, a language model may include a pre-trained language model, such as a language model trained on a corpus of information not specific to applications for selecting agents. In some embodiments, a language model may include a neural network. In some embodiments, a pre-trained language model may be fine-tuned for a specific purpose, such as selection of agents. In some embodiments, low-rank adaptation may be used to fine-tune a neural network.

Still referring to FIG. 1, in some embodiments, a language model may be used to process user input. As used herein, a "language model" is a program capable of interpreting natural language, generating natural language, or both. In some embodiments, a language model may be configured to interpret the output of an automatic speech recognition function and/or an OCR function. A language model may include a neural network. A language model may be trained using a dataset that includes natural language.

Still referring to FIG. 1, in some embodiments, a language model may be configured to extract one or more words from a document. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols. Textual data may be parsed into tokens, which may include a simple word (sequence of letters separated by whitespace) or more generally a sequence of characters. As used herein, a "token," is a smaller, individual grouping of text from a larger source of text. Tokens may be broken up by word, pair of words, sentence, or other delimitations. Tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as chains, for example for use as a Markov chain or Hidden Markov Model.

Still referring to FIG. 1, generating language model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, processor 104 may determine one or more language elements in user input by identifying and/or detecting associations between one or more language elements (including phonemes or phonological elements, morphemes or morphological elements, syntax or syntactic elements, semantics or semantic elements, and pragmatic elements) extracted from at least user input, including without limitation mathematical associations, between such words. Associations between language elements and relationships of such categories to other such term may include, without limitation, mathematical associations, including without limitation statistical correlations between any language element and any other language element and/or Language elements. Processor 104 may compare an input such as a sentence from user input with a list of keywords or a dictionary to identify language elements. For example, processor 104 may identify whitespace and punctuation in a sentence and extract elements comprising a string of letters, numbers or characters occurring adjacent to the whitespace and punctuation. Processor 104 may then compare each of these with a list of keywords or a dictionary. Based on the determined keywords or meanings associated with each of the strings, processor 104 may determine an association between one or more of the extracted strings and a feature of a user input and/or a medical procedure, such as an association between the phrase "QRS complex" and an electrocardiogram. Associations may take the form of statistical correlations and/or mathematical associations, which may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory.

Still referring to FIG. 1, processor 104 may be configured to determine one or more language elements in user input using machine learning. For example, processor 104 may generate the language processing model by any suitable method, including without limitation a natural language processing classification algorithm; language processing model may include a natural language process classification model that enumerates and/or derives statistical relationships between input terms and output terms. An algorithm to generate language processing model may include a stochastic gradient descent algorithm, which may include a method that iteratively optimizes an objective function, such as an objective function representing a statistical estimation of relationships between terms, including relationships between input language elements and output patterns or conversational styles in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word, phrase, and/or other semantic unit. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Still referring to FIG. 1, processor 104 may be configured to determine one or more language elements in user input using machine learning by first creating or receiving language classification training data. Training data may include data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, language classification training data may be a training data set containing associations between language element inputs and associated language element outputs. Language element inputs and outputs may be categorized by communication form such as written language elements, spoken language elements, typed language elements, or language elements communicated in any suitable manner. Language elements may be categorized by component type, such as phonemes or phonological elements, morphemes or morphological elements, syntax or syntactic elements, semantics or semantic elements, and pragmatic elements. Associations may be made between similar communication types of language elements (e.g. associating one written language element with another written language element) or different language elements (e.g. associating a spoken language element with a written representation of the same language element). Associations may be identified between similar communication types of two different language elements, for example written input consisting of the syntactic element "that" may be associated with written phonemes /th/, /ă/, and /t/. Associations may be identified between different communication forms of different language elements. For example, the spoken form of the syntactic element "that" and the associated written phonemes above. Language classification training data may be created using a classifier such as a language classifier. An exemplary classifier may be created, instantiated, and/or run using processor 104, or another computing device. Language classification training data may create associations between any type of language element in any format and other type of language element in any format. Additionally, or alternatively, language classification training data may associate language element input data to a feature related to a user input and/or a medical procedure. For example, language classification training data may associate occurrences of the syntactic elements "where," and "catheter," in a single sentence with a request for data describing a position of a cardiac catheter.

Still referring to FIG. 1, processor 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)\ P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Still referring to FIG. 1, processor 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

Still referring to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, language processing module may use a corpus of documents to generate associations between language elements in a language processing module, and a diagnostic engine may then use such associations to analyze words extracted from one or more documents and determine that the one or more documents indicate significance of a category. In an embodiment, a computing device may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into a computing device. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

Still referring to FIG. 1, in some embodiments, a language model may include a large language model (LLM). A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic health records, entity documents, business documents, inventory documentation, emails, user communications, advertising documents, newspaper articles, and the like. In some embodiments, training sets of an LLM may include information from one or more public or private databases. As a non-limiting example, training sets may include databases associated with an entity. In some embodiments, training sets may include portions of documents associated with the electronic records correlated to examples of outputs. In an embodiment, an LLM may include one or more architectures based on capability requirements of an LLM. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 1, in some embodiments, an LLM may be generally trained. As used in this disclosure, a "generally trained" LLM is an LLM that is trained on a general training set comprising a variety of subject matters, data sets, and fields. In some embodiments, an LLM may be initially generally trained. Additionally, or alternatively, an LLM may be specifically trained. As used in this disclosure, a "specifically trained" LLM is an LLM that is trained on a specific training set, wherein the specific training set includes data including specific correlations for the LLM to learn. As a non-limiting example, an LLM may be generally trained on a general training set, then specifically trained on a specific training set. In an embodiment, specific training of an LLM may be performed using a supervised machine learning process. In some embodiments, generally training an LLM may be performed using an unsupervised machine learning process. As a non-limiting example, specific training set may include information from a database. As a non-limiting example, specific training set may include text related to the users such as user specific data for electronic records correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training.

Still referring to FIG. 1, in some embodiments, a pretrained neural network may be fine-tuned. In some embodiments, a fine-tuning process may include freezing a pretrained weight matrix ($W_0$) of a layer of a pre-trained model and determining an accumulated gradient update ($\Delta W$) of the layer during adaptation of the pre-trained weight matrix. $W_0$ may be a matrix with $W_0 \in R^{d \times k}$. $\Delta W$ may be a matrix with the same dimensions as $W_0$. When running the neural network, a forward pass (h) of a layer may be determined using the formula $h=W_0X+\Delta WX$ where X is the input from a previous layer. In some embodiments, a plurality of layers of a neural network may be fine-tuned. Fine-tuning a pre-trained neural network may improve efficiency of neural network training. In a non-limiting example, a neural network trained on a broad variety of data may be fine-tuned for a specific purpose.

Still referring to FIG. 1, in some embodiments, a pre-trained neural network may be fine-tuned using low rank adaptation. In low rank adaptation, $\Delta W$ is replaced by low rank decomposition matrices A and B, using the formula $\Delta W=BA$. B and A may be matrices with $B \in R^{d \times r}$, and $A \in R^{r \times k}$. Hyperparameter r may represent the rank of a low rank adaptation module and may be chosen such that r<min (d,k) based on factors described below. A forward pass of a layer trained using low rank adaptation may have the formula $h=W_0X+BAX$. A random Gaussian initialization may be used to determine initial values for A and initial values of B may be set to 0, such that $\Delta W=BA$ is 0 before training. $\Delta WX$ may be scaled by $\alpha/r$ during training, where a is a constant in r. In some embodiments, a may be tuned as one would tune a learning rate. In some embodiments, $\alpha$ may be set and not tuned further. In some embodiments, a plurality of layers of a neural network may be fine-tuned using low rank adaptation. Fine-tuning a pre-trained neural network using low-rank adaptation may reduce memory and/or processing power requirements of fine-tuning the neural network, as B and A have fewer trainable parameters than $\Delta W$ would have in a non-low rank adaptation approach. In some embodiments, this difference may lead to substantial improvements where $\Delta W$ has very large dimensions. The value of hyperparameter r may influence the degree to which low rank adaptation reduces memory and/or processing power requirements. In some embodiments, setting r too low may result in information loss. In some embodiments, setting r too high may result in increased memory and processing power usage for fine-tuning the neural network relative to a lower r. In some embodiments, r may be a number of linearly independent rows or columns of $\Delta W$.

With continued reference to FIG. 1, in some embodiments an LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM may include a text prediction based algorithm configured to receive an article and apply a probability distribution to the words already typed in a sentence to work out the most likely word to come next in augmented articles. For example, if some words that have already been typed are "Nice to meet", then it may be highly likely that the word "you" will come next. An LLM may output such predictions by ranking words by likelihood or a prompt parameter. For the example given above, an LLM may score "you" as the most likely, "your" as the next most likely, "his" or "her" next, and the like. An LLM may include an encoder component and a decoder component.

Still referring to FIG. 1, an LLM may include a transformer architecture. In some embodiments, encoder component of an LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, an LLM and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decicer model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM may predict the next word by searching for a set of positions in a source sentence where the most relevant information is concentrated. An LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, attention mechanism may include, without limitation, generalized attention self-attention, multi-head attention, additive attention, global attention, and the like. In generalized attention, when a sequence of words or an image is fed to an LLM, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM may pick up particular parts at different positions in the input sequence and over time compute an initial composition of the output sequence. In multi-head attention, an LLM may include a transformer model of an attention mechanism. Attention mechanisms, as described above, may provide context for any position in the input sequence. For example, if the input data is a natural language sentence, the transformer does not have to process one word at a time. In multi-head attention, computations by an LLM may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM may either attend to all source words or predict the target sentence, thereby attending to a smaller subset of words.

With continued reference to FIG. 1, multi-headed attention in encoder may apply a specific attention mechanism called self-attention. Self-attention allows models such as an LLM or components thereof to associate each word in the input, to other words. As a non-limiting example, an LLM may learn to associate the word "you", with "how" and "are". It's also possible that an LLM learns that words structured in this pattern are typically a question and to respond appropriately. In some embodiments, to achieve self-attention, input may be fed into three distinct fully connected neural network layers to create query, key, and value vectors. A query vector may include an entity's learned representation for comparison to determine attention score. A key vector may include an entity's learned representation for determining the entity's relevance and attention weight. A value vector may include data used to generate output representations. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

Still referencing FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

Continuing to refer to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With further reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens."

Still referring to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

Still referring to FIG. 1, decoder may take this output and add it to the decoder inputs. Decoder may continue decoding until a token is predicted. Decoder may stop decoding once it predicts an end token.

Continuing to refer to FIG. 1, in some embodiment, decoder may be stacked N layers high, with each layer taking in inputs from the encoder and layers before it. Stacking layers may allow an LLM to learn to extract and focus on different combinations of attention from its attention heads.

With continued reference to FIG. 1, an LLM may receive an input. Input may include a string of one or more characters. Inputs may additionally include unstructured data. For example, input may include one or more words, a sentence, a paragraph, a thought, a query, and the like. A "query" for the purposes of the disclosure is a string of characters that poses a question. In some embodiments, an input may include user input 128.

With continued reference to FIG. 1, an LLM may generate at least one annotation as an output. At least one annotation may be any annotation as described herein. In some embodiments, an LLM may include multiple sets of transformer architecture as described above. Output may include a textual output. A "textual output," for the purposes of this disclosure is an output comprising a string of one or more characters. Textual output may include, for example, a plurality of annotations for unstructured data. In some embodiments, textual output may include a phrase or sentence identifying the status of a user query. In some embodiments, textual output may include a sentence or plurality of sentences describing a response to a user query. As a non-limiting example, this may include restrictions, timing, advice, dangers, benefits, and the like.

Still referring to FIG. 1, in some embodiments, system 100 may generate encoded user input 160. As used herein, "encoded user input" is a mathematical representation of user input generated based on relationships between components of the user input. In some embodiments, encoded user input 160 may be generated using a transformer model. In some embodiments, a language model, such as first language model 164, may include a transformer model, may generate an encoded user input, and/or may receive as an input an encoded user input. In some embodiments, generating an agent selection datum as a function of a user input may include inputting into a trained agent selection machine learning model encoded user input 160 and receiving, as an output from the agent selection machine learning model, the first agent selection datum.

Still referring to FIG. 1, in some embodiments, system 100 may generate agent selection datum without first receiving a user input. For example, system 100 may passively monitor a medical procedure and may generate an agent selection datum as a function of data received through such monitoring. Passive monitoring may include, in non-limiting examples, receipt of procedure data 136 and/or electronic health record data 140. For example, system 100 may monitor live ECG data and/or other live procedure data for abnormalities. In some embodiments, a first subset of agents may be used while system 100 is passively monitoring a procedure and a second subset of agents may be activated based on user input 128. In some embodiments, system 100 may determine an agent selection datum during passive monitoring. In some embodiments, determination of an agent selection datum during passive monitoring may include use of agent selection machine learning model. In this instance, an input into agent selection machine learning model may include procedure data such as ECG data, and agent selection machine learning model may output agent selection datum. Such agent selection machine learning model may be trained on a training dataset including example procedure data associated with example agent selection data. In some embodiments, agent orchestrator may match the live procedure data to the corresponding monitoring agent. For example, if live procedure data includes live ECG data, agent orchestrator may determine an agent selection datum corresponding to an ECG monitoring agent. For example, if live procedure data includes live ablation data, agent orchestrator may determine an agent selection datum corresponding to an ablation monitoring agent. The matching of live procedure data to various agents may, in some embodiments, not require the use of machine-learning.

Still referring to FIG. 1, in some embodiments, system 100 may retrain agent selection machine learning model. In some embodiments, system 100 may receive additional training data and may incorporate such training data into a dataset used to retrain agent selection machine learning model. Such dataset may in some embodiments include data of a prior dataset used to train agent selection machine learning model. In some embodiments, such additional training data may be generated based on user feedback. For example, system 100 may generate an agent selection datum and ultimately an output based on a first user input, may receive a second user input indicating a degree to which such output is responsive to the first user input, and system 100 may generate an element of training data as a function of the first user input, the second user input, and/or the output. For example, if second user input indicates that the output was not responsive to the first user input, then a training datum may be generated which may be used to train agent selection machine learning model such that it is less likely to select the same agent when faced with similar user inputs to first user input. In some embodiments, agent selection machine learning model may be trained using reinforcement learning.

Still referring to FIG. 1, in some embodiments, system 100 may, using an agent of plurality of agents 172 which corresponds to an agent selection datum, determine an agent output 168. As used herein, an "agent output" is data generated by an agent. An agent output may include, in non-limiting examples, a 3D model of a structure such as a heart and a Pulsed Field Ablation (PFA) durability datum. In some embodiments, system 100 may input into an agent procedure data 136 and/or at least a portion of electronic health record data 140 and receive, as an output from the agent, agent output 168.

Still referring to FIG. 1, in some embodiments, system 100 may include a plurality of agents and/or may receive multiple agent outputs. In some embodiments, an agent may produce multiple agent outputs based on the same or different user inputs. In some embodiments, different agents may produce different agent responses based on the same or different user inputs. In a non-limiting example, system 100 may generate a first agent selection datum and a first agent output based on a first user input and/or procedure data 136. In this example, system 100 may further receive, from user interface 124, a second user input, receive, from electronic health record database 148, electronic health record data 140, determine, using agent orchestrator 156, a second agent selection datum by generating the second agent selection datum as a function of the second user input using trained agent selection machine learning model, using a second agent corresponding to the second agent selection datum, determine a second agent output by inputting into the second agent the electronic health record data, receive, as an output from the second agent, the second agent output, and display, using the user interface, the second agent output. Such a process may be used to, for example, display information within an electronic health record of a subject as well as display information about an ongoing procedure. In additional examples, a process involving multiple agents may include an agent described below.

Still referring to FIG. 1, in some embodiments, an agent may be used to generate a 3D model of a structure such as a cardiac structure. In some embodiments, an agent may generate a set of shape parameters representing a structure's shape as a function of ultrasonic image data and a shape identification model trained on a training dataset comprising historical ultrasonic images correlated with historical computed tomography scan data and generate a 3D model of the structure based on the set of shape parameters. Agent output 168 may include such 3D model. In some embodiments, such a process may be consistent with U.S. patent application Ser. No. 18/395,087, filed on Dec. 22, 2023, and titled "APPARATUS AND METHOD FOR GENERATING A THREE-DIMENSIONAL (3D) MODEL OF CARDIAC ANATOMY WITH AN OVERLAY," the entirety of which is hereby incorporated by reference.

With continued reference to FIG. 1, an agent may be configured to receive a set of images of a structure of a subject. As used in this disclosure, a "set of images" refers to a group of one or more visual representations. Set of images may include, without limitation, a two-dimensional image. In some embodiments, set of images may include an ultrasonic image. As used herein, an "ultrasonic image" is an image generated as a function of a reflection of a sound wave off of a structure. Non-limiting examples of ultrasonic images and/or imaging techniques include intracardiac echo (ICE) images, transthoracic echocardiograms (TTE), transesophageal echocardiograms (TEE), and point of care ultrasound (POCUS). As used herein, a "structure" is a component of a subject. Non-limiting examples of structures include organs and tissues. In non-limiting examples, a structure may include a heart, lung, spleen, liver, kidney, muscle, skeleton, intestine, stomach, vein, and/or artery. In additional non-limiting examples, a structure may include a left atrium, left atrial appendage, left ventricle, right ventricle, and/or a right atrium.

In an embodiment, set of images may include a set of intracardiac echocardiography (ICE) images. As used herein, a "set of ICE images" is a collection of ultrasound images obtained from within the heart's chambers or blood vessels. In some cases, ICE images may be captured using a specialized catheter equipped with an ultrasound transducer that is inserted into the body and guided to the heart of subject. In an embodiment, set of images may provide a detailed and real-time visualizations of cardiac anatomy. As used herein, "cardiac anatomy" is the structural composition of the heart and its associated blood vessels. Set of images may also include internal structures, functions, and blood flow patterns of the heart of subject. Other exemplary embodiments of set of images may include, without limitation, X-ray images, magnetic resonance imaging (MRI) scans, computed tomography (CT) scans, ultrasound images, optical images, digital photographs, or any other form of visual data. Additionally, images within set of images may be related in terms of content, time of capture, sequence, or any other relevant parameters described herein. In a non-limiting example, each image of set of images may represent a particular view, angle, or perspective of an object, subject, or scene, and may be in two-dimensional (2D) or 3D format. Images of set of images may include, without limitation, any two-dimensional or three-dimensional images of any anatomy or anatomical structure, including without limitation images of any internal organ, tissue including without limitation muscular, connective tissue, epithelial tissue, and/or nervous tissue, bone, and/or any other element that may be imaged within a human and/or animal body.

Still referring to FIG. 1, in a non-limiting example, structure may include chambers (e.g., four chambers including left and right atria and left and right ventricles), valves (i.e., the structures that regulate blood flow between chambers and vessels, including mitral, tricuspid, aortic, and pulmonary valves), vessels (e.g., aorta, pulmonary arteries and veins, and coronary arteries), conduction system (i.e., a network of specialized cells that control the heart's electrical activity and rhythm), muscular and connective tissues (e.g., heart's muscular walls, septa, any other connective tissues that provide structural integrity and enable contraction), LAA and other appendages, pathological features (e.g., any abnormalities, defects, and/or the like), and/or other components of a heart.

Still referring to FIG. 1, as used in this disclosure, a "subject" refers to an individual organism. In an embodiment, subject may include a human, such as a human undergoing a medical procedure such as atrial fibrillation (AF) ablation. In some cases, subject may include a provider of set of images described herein. In other cases, subject may include a recipient or a participant in a clinical trial or research study. In a non-limiting example, subject may include a human patient with AF who is undergoing a procedure, an individual undergoing cardiac screening, a participant in a clinical trial, patient with congenital heart disease, heart transplant candidate, patient receiving follow-up care after cardiac surgery, healthy volunteer, patient with heart failure, or the like. Additionally, or alternatively, subject may include an animal model (i.e., animal used to model AF such as a laboratory rat).

Still referring to FIG. 1, in an embodiment, each ultrasonic image of set of ultrasonic images may include a particular view of subject's heart's chambers, valves, vessel, and/or the like. In a non-limiting example, set of images may include multiple views e.g., different angles and perspectives of subject's heart. In another embodiment, set of images may be arranged in a temporal sequence. In a non-limiting example, set of images may include a series of images captured over time, allowing for an observation of dynamic cardiac functions such as beating, blood flow, and/or the like. In some cases, each ultrasonic image of set of images may include a corresponding timestamp, wherein the timestamp may include an indicator showing a date and time of when the corresponding ultrasonic image was taken.

With continued reference to FIG. 1, an agent may be configured to generate a set of shape parameters based on set of images. As used in this disclosure, a "set of shape parameters" refers to a collection of numerical values or descriptors that quantitatively represent the geometric or morphological characteristics of a structure. In some embodiments, a set of shape parameters may represent a shape of a structure. In a non-limiting example, set of shape parameters may include information and/or metadata calculated, determined, and/or extracted from set of ultrasonic images, such as, dimensions, angles, curvatures, surface areas, texture, symmetry, and/or the like. In other embodiments, agent may be configured to parameterize features (e.g., edges, textures, contours, and any other characteristics that describe the shape structure) extracted from set of images using CNN described herein. Such parameterization may involve agent deriving one or more shape parameters including one or more morphological descriptors that quantitatively describe structure based on extracted features. In some cases, agent may be configured to use principal component analysis (PCA) to reduce the dimensionality of set of shape parameters, allowing agent to focus on the most informative shape parameters of set of shape parameters in further processing steps described below.

With continued reference to FIG. 1, in a non-limiting example, set of shape parameters may be generated based on set of images using machine learning model such as, without limitation, a shape identification model. Generating set of shape parameters may include receiving structure training data, wherein the structure training data may include a plurality of image sets as inputs correlated to a plurality of shape parameter sets as outputs. In some cases, structure training data may be received from a data store. For example, and without limitation, structure training data may be used to show each ultrasonic image may indicate a particular set of shape parameters. In some embodiments, structure training data may include historical ultrasonic images correlated with historical computed tomography scan data. Such a training dataset may be used to train shape identification model to generate a set of shape parameters representing a structure's shape as a function of a set of ultrasonic images, which may be input into the model in order to receive, as an output, a set of shape parameters. Shape identification model may be trained by an agent using structure training data. Additionally, structure training data may include previously input image sets and their corresponding shape parameter outputs. Shape identification model may be iterative such that outputs may be used as future inputs of shape identification model. This may allow the shape identification model to evolve. An agent may be further configured to generate set of shape parameters as a function of set of images using the trained shape identification model.

Still referring to FIG. 1, generating set of shape parameters may include performing image processing/segmentation techniques, as described above, prior to implementation of shape identification model in order to optimize performance and runtime of an agent and training of a model. For example, image segmentation may include normalization and standardization methods performed by computer vision model to ensure that pixel values in images are normalized or standardized to a consistent scale thus aiding convergence during training of shape identification model. Image segmentation may include data augmentation techniques such as rotation, scaling, flipping, and translation to artificially increase the size of the training dataset and improve model generalization. Image segmentation may include image enhancement preprocessing techniques like histogram equalization or contrast stretching to enhance relevant features in the images. Image segmentation may include texture and shape descriptors to extract features beyond pixel values, such as texture and shape descriptors, to capture additional information about structures. Image segmentation may include architecture selection methods, as in experiments with different architectures, such as U-Net, DeepLab, or custom architectures, depending on the complexity and characteristics of the images. Image segmentation may include grid Search or random Search processing methods to systematically explore hyperparameter combinations to find the optimal configuration for a 3D model. As previously disclosed, image segmentation may include separating specific structures or regions of interest (ROI) from the background or other structures in a given ultrasonic image, wherein a collection of ROIs may be also incorporated by the shape parameter training data/structure training data.

With continued reference to FIG. 1, an agent may use a statistical shape model to generate and/or iteratively refine a 3D model based on a set of shape parameters. As used herein, a "3D model," is a 3D representation of a structure. In some embodiments, a 3D model may include a heart model. A heart model may include a 3D representation of cardiac anatomy. In some cases, 3D model may be generated through a direct 3D reconstruction from a series of (2D) ultrasonic images. In a non-limiting example, set of images may include a plurality of ultrasonic images captured from different angles and positions within and/or around a structure. An agent may be configured to apply one or more 3D reconstruction algorithms, such as without limitation, marching cubes, contour detection and segmentation, active contour models, and/or the like to create a coherent 3D representation e.g., 3D model of structure. In some cases, such direct 3D reconstruction may leverage the inherent spatial information within set of images, providing a direct and intuitive way to model the 3D model of a structure. In a further embodiment, generic 3D modeling techniques may be applied to create the initial 3D model. In some cases, generic 3D modeling techniques may include surface modeling, solid modeling, or parametric modeling, among others. As an ordinary person skilled in the art, upon reviewing the entirety of this disclosure, will be aware of various 3D reconstruction algorithms that may be used by an agent to generate 3D model of structure. As used in this disclosure, a "statistical shape model" (SSM) is a data structure representing, including, and/or utilizing a mathematical model that captures principal modes of variation in shape across a population of structures. In some cases, SSM may be constructed by analyzing one or more datasets of shapes and identifying, for example, mean shapes and main modes of variation within the one or more datasets. In a non-limiting example, SSM may start with calculation of at least one mean shape, which represents an average geometry of all shapes of a structure in a given dataset, wherein the at least one mean shape may be served as a central reference point for an agent to understand different variations. In some embodiments, unique SSMs are created for different structure categories, such as different organs or tissues. In a non-limiting example, a first SSM may be created for a first structure category such as kidneys and a second SSM may be created for a second structure category such as hearts. In some cases, dataset may include, without limitation, structure training data, structure training data, and/or any datasets within ultrasonic image databases described herein. SSM may also identify one or more principal modes of variation within given datasets described herein, wherein the "principal modes of variations," for the purpose of this disclosure, refer to main patterns or directions along which data points vary within dataset. In a non-limiting example, identifying principal modes of variations may include applying principal component analysis (PCA) on given dataset. Additionally, or alternatively, shapes may be described directly using plurality of shape parameter sets (in structure training data). In some cases, shape parameter sets may correspond to a plurality of modes of variations. Further, one or more statistical constraints (e.g., mean, variance, correlation, boundary, proportion constraint and/or the like) may be introduced into SSM based on the distribution of shape parameters within plurality of shape parameter sets and/or 3D structure dimensions. In some embodiments, each shape parameter within a set of shape parameters may be associated with and/or comprise a corresponding parameter range. Such a parameter range may, for example, include a range of values associated with a normal and/or healthy structure. Such a parameter range may be determined based on, for example, a subset of possible values of a parameter which historical healthy structures commonly fall into, as determined from a dataset.

With continued reference to FIG. 1, in some cases, once modes of variation are extracted, an agent may be configured to create a shape representation for any given structure shape within the studied class. In a non-limiting example, 3D model having a shape S may be mathematically represented as $S = \bar{S} + \Sigma_{k=1}^{M} a_k \times \phi_k$, wherein $\bar{S}$ denotes the mean shape derived from the set of example shapes, M is the number of modes of variation considered, $a_k$ are the coefficients or weights for each mode, and $\phi_k$ are the modes of variation (eigenvectors corresponding to the kth principal component). In some cases, coefficients $a_k$ may dictate a degree to which each mode of variation is present in shape S. In some cases, coefficients $a_k$ may vary from positive to negative (or negative to positive) based on the deformation of the 3D model in directions described by each mode of variation. In some cases, 3D model may include mean shape as described herein. In some cases, 3D model may include a predictive structure shape that may not have been explicitly seen in the set of example shapes or patient's heart observations. In some cases, 3D model may be in 3D VOR as described above.

Still Referring to FIG. 1, an agent may be configured to generate a map regarding one or more levels of uncertainty. A "map," as used herein, refers to a visualization. Map may include level(s) of uncertainty to be visualized on the 3D model. Map may include a color-coded heatmap, including other visual cues, symbols or indicators that alert a user to areas of 3D model that may require extra caution when used for planning or guidance during a medical procedure. For example, after obtaining the segmentation results from 3D model, map may be generated. Map may highlight the uncertainty or confidence level associated with each pixel in the segmentation. Assigning colors to different intensity levels in map allows for an intuitive visualization. Typically, warmer colors (e.g., red, or yellow) might represent high uncertainty, while cooler colors (e.g., blue, or green) could indicate low uncertainty. The color-coding can be adjusted based on specific thresholds or clinical requirements.

Still referring to FIG. 1, generating map may include methods such as Class Activation Mapping (CAM). Class Activation Mapping is a technique that originated for image classification tasks and has been extended to provide visual insights into the regions of an image that are most important for a particular class. CAM allows the visualization of the spatial attention of a convolutional neural network (CNN) by generating heat maps that highlight discriminative regions. CAM may be applied to the last convolutional layer of a CNN. The features extracted by this layer capture high-level semantic information, making it suitable for visualizing the importance of different regions in an image. CAM is typically applied to the last convolutional layer of a CNN. The features extracted by this layer capture high-level semantic information, making it suitable for visualizing the importance of different regions in an image. The output of the global average pooling is then fed into a fully connected layer with a softmax activation function. This converts the features into class scores, indicating the likelihood of the image belonging to different classes. The CAM algorithm computes a weighted sum of the original feature maps based on the weights of the fully connected layer. These weights are determined during the training process and represent the importance of each feature map for a specific class. The weighted sum is applied to the original feature maps, producing a single heat map. This heat map highlights the regions of the input image that contributed most to the prediction for the target class. The generated heat map can be overlaid on the input image, visually indicating which regions are most relevant for the predicted class. Typically, warmer colors (e.g., red, or yellow) represent higher activation or importance.

Still Referring to FIG. 1, generating map may include Grad-CAM (Gradient-weighted Class Activation Mapping). Grad-CAM is an extension of Class Activation Mapping (CAM) that enhances the localization capabilities by incorporating gradient information from the final convolutional layer of a neural network. Grad-CAM helps to generate heat maps that highlight discriminative regions in an image, providing more fine-grained insights into where a convolutional neural network (CNN) is focusing its attention when making predictions. In traditional CAM, the last convolutional layer's feature maps are linearly combined to obtain a weighted sum, and the resulting weights are used to create a heat map that highlights relevant regions for a specific class. Grad-CAM improves upon CAM by introducing gradient information. It computes the gradients of the predicted class score with respect to the feature maps of the last convolutional layer. Grad-CAM retains the global average pooling (GAP) operation applied after the last convolutional layer, as it is an integral part of CAM. The GAP operation condenses the spatial information into a single value per feature map. The gradients obtained in the previous step are used to calculate the importance of each feature map. These gradients represent the importance of each feature map in contributing to the final prediction. A weighted sum is computed using these gradients, and this is combined with the original feature maps. The computed sum goes through a ReLU activation function, discarding any negative values. This step emphasizes positive contributions and suppresses negative ones. The ReLU-activated weighted sum is linearly combined with the original feature maps to produce a weighted combination. This combination retains spatial information and helps create a more accurate heat map. The resulting heat map is often normalized to enhance visualization, ensuring that the values are within a specific range (e.g., between 0 and 1). The final heat map generated by Grad-CAM is then overlaid on the input image, highlighting the regions of interest for the predicted class. The intensity of the heat map indicates the importance of different regions. Grad-CAM enhances the interpretability and explainability of deep learning models, allowing practitioners and researchers to understand which parts of an image are crucial for a particular prediction. This is particularly valuable in applications such as medical imaging or any domain where understanding the decision-making process is critical.

Still Referring to FIG. 1, generating map may include utilizing a "SmoothGrad technique," a technique designed to improve the interpretability of neural network predictions by reducing the noise in the attribution maps or heat maps generated by visualizing gradients. It is particularly useful for understanding the decision-making process of deep learning models, especially in scenarios where the explanations need to be robust and less sensitive to input perturbations. The primary goal of SmoothGrad is to enhance the visual quality of attribution maps generated by visualizing gradients. Attribution maps highlight the regions in the input that contribute most to a model's prediction. SmoothGrad aims to reduce the impact of noise in these maps, providing more stable and interpretable visualizations. The key idea behind SmoothGrad is to introduce perturbations to the input data. Instead of attributing the prediction solely to the gradients calculated with respect to the original input, the gradients are averaged over multiple perturbed versions of the input. By averaging the gradients over multiple perturbed samples, SmoothGrad helps reduce the impact of noise or irrelevant features in the attribution maps. This is particularly beneficial when dealing with complex or noisy datasets. Perturbation techniques include adding Gaussian noise, random rotations, or random translations to the input data. These perturbations create variations in the input while preserving the essential features, leading to more stable and reliable attribution maps. For each perturbed input, gradients are calculated with respect to the model's output. These gradients are then averaged over all perturbed samples. This process smoothens the attribution map by reducing the influence of random noise. The averaged gradients may undergo normalization or scaling to ensure that the values are interpretable and within a specific range. This step can enhance the consistency and comparability of the generated attribution maps. The final step involves generating a heat map using the smoothed gradients. The heat map represents the attribution of different regions in the input to the model's prediction, providing a clearer and more stable visualization.

Still Referring to FIG. 1, generating map may include implementing one or more Gaussian Processes. A Gaussian Process is a collection of random variables, any finite subset of which has a joint Gaussian distribution. In simpler terms, it's a distribution over functions rather than a distribution over finite-dimensional vectors. Gaussian Processes (GPs) can be applied to generate heat maps in various ways, particularly in the context of regression tasks where one would want to predict continuous values across a spatial domain. Given a set of observed data points, the GP can predict the values at unobserved locations in the spatial domain. Importantly, it also provides uncertainty estimates associated with these predictions. This uncertainty can be visualized as a heat map. The predicted values from the GP represent the main heat map, indicating the expected values across the spatial domain. The uncertainty associated with each prediction can be visualized as an uncertainty heat map. This uncertainty heat map provides insights into regions where the model is less confident about its predictions. Overlay of the main heat map and the uncertainty heat map on the original spatial data may create a composite visualization. Warmer colors in the main heat map might represent higher predicted values, while the uncertainty heat map's intensity could indicate regions where the model's predictions are less certain.

Still referring to FIG. 1, in some embodiments, an agent may be used to generate a Pulsed Field Ablation (PFA) durability datum. In some embodiments, an agent may include a lesion durability agent. As used herein, a "lesion durability agent" is an agent configured to generate a PFA durability datum. In some embodiments, a lesion durability agent may generate a PFA durability datum as a function of a PFA device parameter using a trained PFA durability machine learning model. In some embodiments, an agent output may include such PFA durability datum. In some embodiments, procedure data may include a Pulsed Field Ablation (PFA) device parameter and an agent may determine the agent output 168 by generating a PFA durability datum as a function of the PFA device parameter using a trained PFA durability machine learning model. In some embodiments, such a process may be consistent with U.S. patent application Ser. No. 18/646,991, filed on Apr. 26, 2024, and titled "METHOD AND APPARATUS FOR PREDICTING PULSED FIELD ABLATION DURABILITY," the entirety of which is hereby incorporated by reference.

Still referring to FIG. 1, in some embodiments, an agent may receive PFA data. As used herein, "PFA data" is medical data of a subject which undergoes PFA, including PFA device parameters. PFA includes the delivery of rapid high voltage pulsed electrical fields to tissue, such as cardiac tissue. This may cause electroporation of cell membranes in the affected tissue. In some embodiments, PFA may include irreversible electroporation, in which pores are created in cell membranes, leading to cell death. In some embodiments, the strength of the effect applied may be controlled such that only target tissues are destroyed, and not surrounding tissues. In some embodiments, surrounding tissues around a target tissue may have higher thresholds for damage from electroporation. PFA may be applied to subject, and PFA data of subject may be determined. In some embodiments, PFA may be applied in subject with Atrial Fibrillation (AFib).

Still referring to FIG. 1, in some embodiments, PFA data may include PFA device parameter. As used herein, a "PFA device parameter" is an input variable that can be used to control output of a PFA device. As used herein, a "PFA device" is a device used to perform pulse field ablation of tissue, e.g., cardiac tissue. Non-limiting examples of PFA device include the FARAPULSE PFA System (Boston Scientific) and PulseSelect (Medtronic). Non-limiting examples of PFA device parameters include voltage, pulse duration, frequency, pulse width, amplitude, power of ablation, total energy delivered, total treatment time, energy delivered to a particular location, treatment time at a particular location, current, average power, peak power, and pulse delivery phase (e.g., biphasic vs monophasic pulse delivery). In some embodiments, a PFA device parameter may be selected from the list consisting of voltage, pulse duration, frequency, pulse width, amplitude, power of ablation, total energy delivered, total treatment time, energy delivered to a particular location, treatment time at a particular location, current, average power, peak power, and biphasic vs monophasic pulse delivery. In some embodiments, PFA data may include a PFA device identifier. As used herein, a "PFA device identifier" is a representation of a type of PFA device used to perform PFA in a subject. In some embodiments, PFA data may include an electrode configuration used to apply PFA. In some embodiments, PFA data may include a location of one or more electrodes during PFA. In some embodiments, PFA device parameter may include a parameter that has been used, is about to be used, and/or could be used at a PFA device. In some embodiments, an agent may receive from PFA device PFA device parameter. In some embodiments, an agent may input into PFA device a PFA device parameter. For example, a PFA device parameter may be generated, optimized and/or modified based on a function described herein, and a result may be transmitted to PFA device for use in a PFA procedure.

Still referring to FIG. 1, in some embodiments, PFA data may include electrocardiogram (ECG) datum. As used herein, an "ECG datum" is a datum describing electrical activity of a heart. Likewise, "ECG data" is data describing electrical activity of a heart. In some embodiments, an ECG datum may include a rhythm strip ECG datum. As used herein, a "rhythm strip ECG datum" is a datum describing electrical activity detected using a single electrode. In some embodiments, an ECG datum may include a median beat ECG datum. As used herein, a "median beat ECG datum" is a datum describing electrical activity detected using a plurality of leads and/or electrodes. In some embodiments, ECG datum may include data collected by 2, 3, 4, 5, 6, 7, 8, 9, 10, 11, 12, or more ECG leads. For example, ECG datum may include a median beat collected by 12 ECG leads. In some embodiments, ECG datum may be associated with subject. In some embodiments, ECG datum may be detected and/or recorded using ECG sensor. ECG sensor may include one or more electrodes. Electrodes may be placed on subject such as on chest, arms, and legs of subject. Electrodes may detect electrical impulses produced by the heart. Lead wires may be used to connect electrodes to a computing device of an ECG sensor. ECG sensor may receive electrical signals from electrodes, may amplify such signals and convert them into a visual representation, such as a waveform. ECG sensor may include one or more lead wires. As used herein, an "ECG sensor" is a device configured to measure the electrical activity of a heart. ECG sensor may include a device configured to measure and/or interpret electrical activity of heart of subject using electrodes and/or lead wires. In some embodiments, ECG sensor may be configured to detect ECG datum and/or transmit ECG datum to an agent. In some embodiments, ECG sensor may include a surface ECG sensor. In some embodiments, ECG sensor may include an intracardiac ECG sensor.

Still referring to FIG. 1, in some embodiments, PFA data may include image data. Such image data may include cardiac image data. Cardiac image data may be obtained by, in non-limiting examples, echocardiogram, cardiac computed tomography, nuclear cardiac stress test, single-photon emission computed tomography, cardiac positron emission tomography, coronary angiogram, cardiac MRI, and multigated acquisition scan.

Still referring to FIG. 1, in some embodiments, an agent may generate PFA durability datum as a function of PFA data using a trained PFA durability machine learning model. As used in this disclosure, a "PFA durability machine learning model" is any machine-learning model, process, or algorithm that outputs a PFA durability datum. As used herein, a "PFA durability datum" is a representation of PFA durability, for example measurement, quantification, prediction, estimate, and/or probability of PFA durability. As used herein, "PFA durability" is a tendency for tissue treated with pulsed field ablation to remain affected by the pulse field ablation, e.g., stay dead. PFA durability machine learning model may be trained using a supervised learning algorithm. PFA durability machine learning model may be trained on training data including example PFA data, associated with example PFA outcomes. As used in this disclosure, a "PFA outcome" is used to describe both (1) physiological results of PFA procedures; and (2) representation of these results. PFA outcomes may be represented according to medical device measurements (e.g., ECG), doctor notes, patient accounts, and the like. In some cases, example PFA data may include example PFA device parameters. Once PFA durability machine learning model is trained, it may be used to determine PFA durability datum. An agent may input PFA data into PFA durability machine learning model, and an agent may receive PFA durability datum from the model. In a non-limiting example, PFA durability machine learning model may be trained on a training dataset including example PFA device parameters associated with example PFA outcomes, and PFA durability machine learning model may accept as an input PFA device parameter. In another non-limiting example, PFA durability machine learning model may be trained on a training dataset including example ECG data associated with example PFA outcomes, and PFA durability machine learning model may accept as an input ECG datum. In some embodiments, training dataset for PFA durability machine-learning model may include ECG data and/or electrogram (EGM) data correlated to PFA outcomes. In some embodiments, training dataset for PFA may include in-procedure ECG data and/or in-procedure electrogram data correlated to PFA outcomes. For the purposes of this disclosure, "in-procedure ECG data" refers to data that is collected using an ECG during an ablation procedure. For the purposes of this disclosure, "in-procedure EGM data" refers to data that is collected using an EGM during an ablation procedure. In some embodiments, PFA durability machine learning model may include a fused classifier ensemble machine learning model. For example, the output of one or more classifiers may be used as inputs in another machine learning step. Such a system may use gradient boosting, such as, in a non-limiting example, CatBoost. In some embodiments, PFA durability machine learning model may include a 1-dimensional convolutional neural network, such as, in a non-limiting example, U-Net. In some embodiments a 1-dimensional convolutional neural network may be used to interpret intracardiac voltage and/or surface voltage input data. In some embodiments, PFA durability machine learning model may include a 2-dimensional convolutional neural network. In a non-limiting example, a 2-dimensional convolutional neural network may be used to interpret CT scans and/or MRI scans to create classifications between geometric surfaces which may be predictive of Afib recurrence.

Still referring to FIG. 1, in some embodiments, PFA durability datum may include a likelihood and/or probability that a lesion is predicted to be durable. In some embodiments, a probability that a lesion is predicted to be durable is expressed as a number from 0 to 1. In some embodiments, a probability that a lesion is predicted to be durable is expressed as a percentage. In some embodiments, PFA durability datum may include a length of time over which a lesion is predicted to be durable. In some embodiments, PFA durability datum may include a Boolean variable representing whether or not a lesion is predicted to be durable. In some embodiments, PFA durability datum represented on a continuum may be mapped to one or more fuzzy sets representing values of linguistic variables.

Still referring to FIG. 1, in some embodiments, example PFA outcomes may be determined from patient medical records. Example PFA outcomes may include diagnoses, such as whether AFib recurred and/or resolved, and ECG data, such as ECG data of a form described above. In some embodiments, example PFA outcomes may be determined from image data, such as image data generated using, in non-limiting examples, echocardiogram, cardiac computed tomography, nuclear cardiac stress test, single-photon emission computed tomography, cardiac positron emission tomography, coronary angiogram, cardiac MRI, and multigated acquisition scan. In some embodiments, example PFA outcomes may be determined using intracardiac echocardiography (ICE). In some cases, example PFA outcomes may include a date of recurrence of AFib and/or a date of reperformed ablation. In some embodiments, such dates may be measured in absolute terms and/or in terms relative to a date of a PFA procedure. In some embodiments, PFA outcome data may include an AFib burden. As used herein, an "AFib burden data" is a representation of AFib experienced by a subject, for example quantity of Afib, quality of Afib, or both. In some embodiments, low AFib burden may correlate with positive example PFA outcomes as, in some cases, minor occasional AFib may not warrant a second cardiac ablation, for example. In some embodiments, example PFA data may include historical PFA data in a form described above and/or gathered as described above with respect to PFA data. In some embodiments, example PFA outcomes may be determined based on medical data of subjects captured after such subjects undergo PFA. In a non-limiting example, example PFA outcomes may include historical post-PFA procedure ECG data. As used in this disclosure, "post-PFA procedure ECG data" is a representation of an any electrocardiogram-type of measurement taken on a subject, at any time, after a pulse field ablation procedure. Additional detail with respect to timing of data gathering is provided below. In some embodiments, example PFA outcomes may be categorical, such as positive or negative outcome. In some embodiments, example PFA outcomes may have a numerical value, such as a value within a range where values on one end of the range indicate positive outcomes and values on the other end of the range indicate negative outcomes.

Still referring to FIG. 1, in some embodiments, an agent may be used to process an electrocardiogram (ECG) datum, such as by determining a signal metric based on the ECG datum. In some embodiments, system 100 may receive, from user interface 124, user input 128, receive an ECG datum, determine, using agent orchestrator 156, an agent selection datum by generating the agent selection datum as a function of user input 128 using a trained agent selection machine learning model, using an agent corresponding to the agent selection datum, determine agent output 168 by inputting into the third agent the ECG datum, and receiving, as an output from the agent, a signal metric, and display, using user interface 124, the signal metric.

Still referring to FIG. 1, in the context of ECG data, a signal may include a physical record of medical data of a subject. In some embodiments, signal may include a paper readout of medical data produced by a device which records such data from a sensor. Signal may include, in non-limiting examples, electrocardiogram (ECG) data, electroencephalogram (EEG) data, X-ray data, MRI data, CT scan data, and pathology test data. In a non-limiting example, signal may include a physical printout of such data. In some embodiments, signal may include a measurement of activity of a subject's heart. In some embodiments, signal may include ECG data. In some embodiments, signal may include time series data. In some embodiments, signal may include a plurality of parallel recordings of time-series data, such as in a 12 lead ECG.

Still referring to FIG. 1, in some embodiments, an agent may determine signal metric as a function of an image. As used herein, a "signal metric" is a measurement of a signal, a measurement of a feature of a signal, or both. In non-limiting examples, where a signal includes ECG data, a signal metric may include a measurement of a PR interval, RR interval, ST interval, TP interval, QT interval, P wave duration, PR segment, QRS duration, ST segment, P axis, and number of beats per minute. In another example, where a signal includes ECG data, a signal metric may include a rhythm type, such as a sinus rhythm. In some embodiments, signal metric is selected from the list consisting of a PR interval, a QRS duration, a P axis, and a number of beats per minute. In a non-limiting example, signal metric may include a measurement of a first feature of a signal relative to a second feature of a signal. Signal metric may be determined using a machine vision system. For example, a machine vision system may be used to determine one or more peaks of ECG data, and a distance between peaks may be used to determine an RR interval. In another example, a machine vision system may be used to determine a slope of one or more points and/or segments of ECG data and/or rate of change of such a slope, and such data may be used to determine a QRS duration. In some embodiments, signal metric may be determined using a signal metric machine learning model. In some embodiments, a signal metric machine learning model may be trained using a supervised learning algorithm. A signal metric machine learning model may be trained on a training dataset including example images, associated with example signal metrics. Such a training dataset may be generated by, for example, collecting images of signals, and associating them with historical signal metrics manually determined by specialists based on those signals. In some embodiments, generation of signal metric may include embedding image. Embedding image may include generation of a numerical representation of image. In some embodiments, such a numerical representation may include a vector, where similarity between vectors across multiple inputs indicate similarity between inputs. In some embodiments, a machine learning model, such as a convolutional neural network, may be used to create such a numerical representation. Non-limiting examples of convolutional neural networks for embedding image data include VGG (Visual Geometry Group), ResNet (Residual Networks), Inception (GoogLeNet) and EfficientNet. In some embodiments, one or more preprocessing steps may be applied prior to embedding image. For example, image may be resized and/or normalized in order to make it suitable for input into a machine learning model trained to generate an embedding. In some embodiments, embedding image data may be used to reduce dimensionality of high dimensional data. In some embodiments, embedding image data may be used to extract features from image data. In some embodiments, an embedding may be input into signal metric machine learning model, and signal metric may be received as an output.

Still referring to FIG. 1, in some embodiments, an agent may determine signal metric position as a function of signal metric. As used herein, a "signal metric position" is a data structure describing the position of a signal metric relative to that of one or more members of a population. As a non-limiting example, a signal metric position may indicate that a subject's PR interval is higher than 55% of a population. In some embodiments, a population restriction may be identified, and a population which a user's signal metric is compared to may be determined according to a population restriction. As used herein, a "population restriction" is a data structure setting a boundary on individuals to be considered members of a population. In non-limiting examples, population restrictions may include a limitation that members of a population be male, and a limitation that members of a population be under 25 years old. In a non-limiting example, determination of signal metric position may include the following steps: determination of signal metric as described herein, retrieval of a plurality of instances of a like metric of members of a population conforming to a population restriction or retrieval of data describing a distribution of such metric among members of a population, and comparison of signal metric to such metrics. In some embodiments, retrieval of a like metric of members of a population and/or retrieval of data describing a distribution of such metric may include generation of a query requesting such information from a database, such as repository, transmission of such query to repository, and receipt of a response. In a non-limiting example, signal metric may be compared to like metrics of members of a population in order to determine a percentage of like metrics which signal metric is above.

Still referring to FIG. 1, in some embodiments, an agent may generate abnormality datum. In some embodiments, abnormality datum may be generated as a function of image. As used herein, an "abnormality datum" is a data structure describing a difference between a signal and a typical signal of a healthy individual. In a non-limiting example, abnormality datum may include an amount a subject's at rest heart rate is above an at rest heart rate of a healthy individual. In some embodiments, abnormality datum may be determined as a function of signal metric and/or signal metric position. In some embodiments, an agent may generate abnormality datum based on signal metric being above or below a threshold. A threshold may be determined as a function of information about a subject associated with signal, such as age, sex, medical history, and the like. In another non-limiting example, an agent may generate abnormality datum based on signal metric position being above or below a threshold. In a non-limiting example, an agent may generate abnormality datum if signal metric position indicates that signal metric is in the top 5% of a population. In some embodiments, system 100 may display an abnormality datum using user interface 124.

Still referring to FIG. 1, in some embodiments, an agent may determine medical condition datum. As used herein, a "medical condition datum" is a data structure identifying in a subject an ailment, a lack of an ailment, a likelihood of an ailment, or a combination thereof. For example, medical condition datum may indicate that a subject has a particular disease. In another example, medical condition datum may indicate that a subject does not have a particular disease. In another example, medical condition datum may indicate that a subject is healthy. In another example, medical condition datum may indicate that a subject has a first disease and does not have a second disease. In another example, medical condition datum may indicate that a subject has a high likelihood of having a particular disease. Diseases which medical condition datum may identify include, in non-limiting examples, an infectious disease, a deficiency disease, a hereditary disease, and a physiological disease. In some embodiments, an agent may display medical condition datum to user. Display of information to a user is described below.

Still referring to FIG. 1, in some embodiments, an agent may determine medical condition datum by identifying a similarity between signal metric and deidentified patient health information of repository and generating medical condition datum as a function of the similarity. As used herein, a "similarity" between a first datum and a second datum is a data structure describing the numerical distance between the first datum and the second datum, a data structure describing whether the first datum and the second datum are members of the same category, or both. As a non-limiting example, a similarity may include a comparison between a first subject's heart rate while resting with heart rates while resting of a population. In some embodiments, a similarity may be determined between abnormality datum and deidentified patient health information of repository, and medical condition datum may be generated as a function of such similarity. In some embodiments, a similarity may be determined which accounts for multiple signal metrics and/or other information relating to a subject such as age, sex, ethnicity, levels of physical activity, diet, medications the subject is on, and other aspects of subject's medical history. In a non-limiting example, an agent may determine signal metric from signal, query repository for deidentified patient health information with metrics within a range of signal metric, receive deidentified patient health information from repository, and determine medical condition datum as a function of medical conditions of received deidentified patient health information.

Still referring to FIG. 1, in some embodiments, an agent may generate medical condition datum using a medical condition machine learning model. Medical condition machine learning model may be trained using a supervised learning algorithm. Medical condition machine learning model may be trained on a training dataset including example images, signal metrics, abnormality data, and/or calibration data, associated with example medical conditions. Such a training dataset may be obtained by, for example, gathering diagnoses of historical subjects and associating those diagnoses with images of ECG data of those subjects. Once medical condition machine learning model is trained, it may be used to determine medical condition datum. An agent may input image, signal metric, calibration datum, and/or abnormality datum into medical condition machine learning model, and an agent may receive medical condition datum from the model.

Still referring to FIG. 1, in some embodiments, an agent may generate medical condition confidence score. In some embodiments, medical condition machine learning model may output medical condition confidence score in addition to its other outputs. As used herein, a "confidence score" is a degree of confidence that an associated datum is accurate. As used herein, a "medical condition confidence score" is a degree of confidence that a medical condition datum is accurate. In some embodiments, a confidence score may be determined as a function of a machine learning model, such as medical condition machine learning model. Confidence scores may be used to predict how likely a model output is to be accurate. For example, in some classifiers, numerical values are calculated, and a cutoff value is used to determine which category the input fits into. In this example, the numerical value may be used to determine a certainty score based on how closely it fits into a class and/or how close to a decision boundary it is. In another example, in clustering algorithms, certainty scores may be calculated based on how closely an input fits into a cluster. In some embodiments, medical condition datum may be generated without the use of medical condition machine learning model, and medical condition confidence score may be generated using other methods. For example, where medical condition datum is determined as a function of a comparison between signal metric and a threshold, medical condition confidence score may be determined as a function of the distance between signal metric and the threshold. In a non-limiting example, signal may include ECG data, signal metric may include a prediction of a subject's left ventricular ejection fraction (LVEF) based on such ECG data, and abnormality datum may be determined based on a comparison between the LVEF prediction and a threshold. For example, abnormality datum may be determined if such LVEF prediction is below a threshold.

Still referring to FIG. 1, in some embodiments, an agent may select medical condition machine learning model from a plurality of medical condition machine learning models. In some embodiments, such selection may be performed as a function of calibration datum. In a non-limiting example, different medical condition machine learning models may be applied to images of different signal types, and calibration datum may indicate a type of signal that image depicts (such as ECG data), such as based on user input.

Still referring to FIG. 1, in some embodiments, an agent may identify guidance on treatment of a medical condition as a function of medical condition datum. For example, an agent may retrieve from a database guidance on best practices for treatment and/or prevention of a medical condition associated with medical condition datum. In some embodiments, retrieved guidance may include guidance published by a relevant medical association. In some embodiments, an agent may identify guidance using a web search, such as a keyword search. In some embodiments, an agent may identify guidance using a machine learning model, such as a language model trained on medical publications. Guidance on treatment of a medical condition may be displayed to user.

Still referring to FIG. 1, in some embodiments, an agent may generate quality diagnostic of image. In some embodiments, quality diagnostic is generated by extracting a plurality of signal metrics from signal; validating signal by classifying signal to a plurality of preliminary signal metrics; and determining an accuracy status of the extracted plurality of signal metrics by comparing the plurality of preliminary signal metrics to the extracted plurality of signal metrics; and generating the quality diagnostic based on validation of signal. In some embodiments, quality diagnostic may identify an error in a medical procedure used to record signal, and/or an error in another step such as capturing of image of signal, and/or processing of image. In some embodiments, an agent may alert user as to an error identified by quality diagnostic. This may allow user to, for example, record a new, more accurate, set of data. For example, an agent may capture a second image of signal as a function of quality diagnostic.

Still referring to FIG. 1, in some embodiments, system 100 may display agent output 168. In some embodiments, system 100 may display agent output 168 using user interface 124. In some embodiments, first agent output may include converting agent output 168 to audio output data and outputting the audio output data using user interface 124. This may be performed using, for example, a text to speech system. In some embodiments, agent output 168 may be modified prior to being output, such as by converting agent output 168 to a natural language response 176 and displaying natural language response 176 using user interface 124. In some embodiments, natural language response 176 may be generated using second language model 180 based on agent output 168. Language models are described above.

Still referring to FIG. 1, in some embodiments, a visual element data structure may include a visual element. As used herein, a "visual element" is a datum that is displayed visually to a user. In some embodiments, a visual element data structure may include a rule for displaying visual element. In some embodiments, a visual element data structure may be determined as a function of agent output 168 and/or natural language response 176. In some embodiments, a visual element data structure may be determined as a function of an item from the list consisting of user input 128, multimodal data 132, procedure data 136, electronic health record data 140, one or more agents of plurality of agents 172, agent output 168, and/or natural language response 176. In a non-limiting example, a visual element data structure may be generated such that visual element describing or highlighting agent output 168 and/or natural language response 176 is displayed to a user. In a non-limiting example, a visual element may include an electronic health record including medical test results of a subject.

Still referring to FIG. 1, in some embodiments, visual element may include one or more elements of text, images, shapes, charts, particle effects, interactable features, and the like. In a non-limiting example, system 100 may include an element which a user may interact with in order to provide feedback to system 100 on a relevance of an output.

Still referring to FIG. 1, a visual element data structure may include rules governing if or when visual element is displayed. In a non-limiting example, a visual element data structure may include a rule causing a visual element describing agent output 168 and/or natural language response 176 to be displayed when a user selects agent output 168 and/or natural language response 176 using a graphical user interface (GUI).

Still referring to FIG. 1, a visual element data structure may include rules for presenting more than one visual element, or more than one visual element at a time. In an embodiment, about 1, 2, 3, 4, 5, 10, 20, or 50 visual elements are displayed simultaneously.

Still referring to FIG. 1, a visual element data structure rule may apply to a single visual element or datum, or to more than one visual element or datum. For example, a visual element data structure may rank visual elements and/or other data and/or apply numerical values to them, and a computing device may display a visual element as a function of such rankings and/or numerical values. A visual element data structure may apply rules based on a comparison between such a ranking or numerical value and a threshold.

Still referring to FIG. 1, in some embodiments, visual element may be interacted with. For example, visual element may include an interface, such as a button or menu. In some embodiments, visual element may be interacted with using a user device such as a smartphone.

Still referring to FIG. 1, in some embodiments, system 100 may transmit visual element to a display. A display may communicate visual element to user. A display may include, for example, a smartphone screen, a computer screen, or a tablet screen. A display may be configured to provide a visual interface. A visual interface may include one or more virtual interactive elements such as, without limitation, buttons, menus, and the like. A display may include one or more physical interactive elements, such as buttons, a computer mouse, or a touchscreen, that allow user to input data into the display. Interactive elements may be configured to enable interaction between a user and a computing device. In some embodiments, a visual element data structure is determined as a function of data input by user into a display.

Still referring to FIG. 1, in some embodiments, a system and/or method described herein may improve a process by which a medical professional may receive data relevant to an ongoing medical procedure. For example, input using voice commands may allow a user to receive data while occupied with another task. In another example, an ability to call multiple agents may improve versatility of system 100. In some embodiments, use of a language model selection of an agent may allow inputs to be received in a manner not dependent on specific language and/or commands, but using a more natural form of speech.

Figure 2:
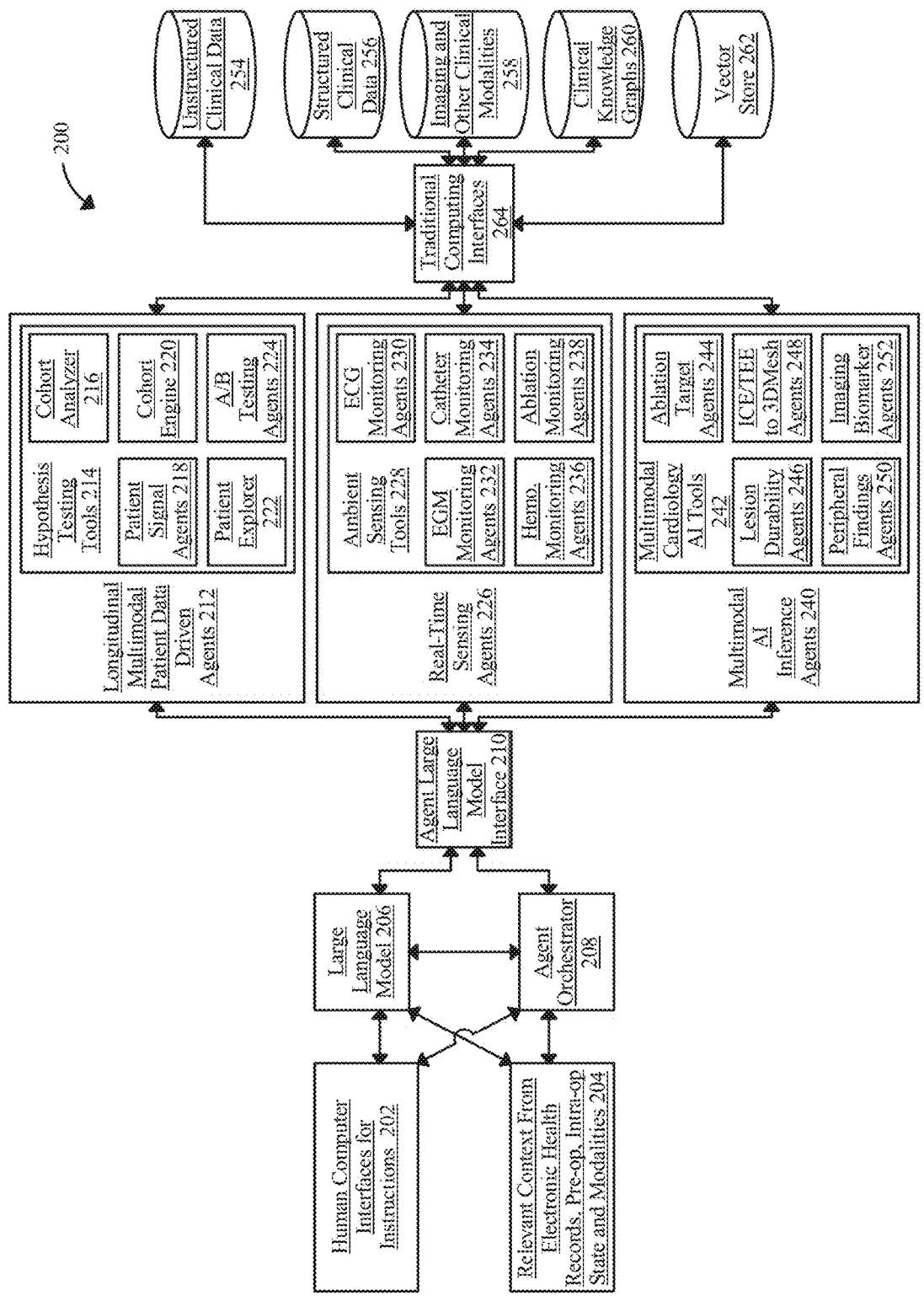
FIG. 2 is a diagram depicting an exemplary embodiment of a system for including an agent orchestrator.

Referring now to FIG. 2, an exemplary embodiment of a system 200 including an agent orchestrator is provided. System 200 may include one or more human computer interfaces 202. Such human computer interfaces may be used to receive instructions for system 200. System 200 may receive relevant context 204 from electronic health records, pre-op, intra-op state and modalities. Instructions and/or context may be input into large language model 206 and/or agent orchestrator 208, which may interact with agents using agent large language model interface 210.

Still referring to FIG. 2, in some embodiments, system 200 may include longitudinal multimodal patient data driven agents 212, which may include hypothesis testing tools 214 such as cohort analyzer 216, patient signal agents 218, cohort engine 220, patient explorer 222, and/or A/B testing agents 224. In some embodiments, system 200 may include real-time sensing agents 226 which may include ambient sensing tools 228 such as ECG monitoring agents 230, EGM monitoring agents 232, catheter monitoring agents 234, hemodynamic monitoring agents 236, and/or ablation monitoring agents 238. In some embodiments, system 200 may include multimodal AI inference agents 240 which may include multimodal cardiology AI tools 242 such as ablation target agents 244, lesion durability 246, ICE/TEE to 3DMesh agents 248, peripheral findings agents 250, and/or imaging biomarker agents 252.

Still referring to FIG. 2, in some embodiments, one or more agents may interact with and/or receive unstructured clinical data 254, structured clinical data 256, imaging and other clinical modalities 258, clinical knowledge graphs 260 and/or vector store 262 using traditional computing interfaces 264.

Figure 3:
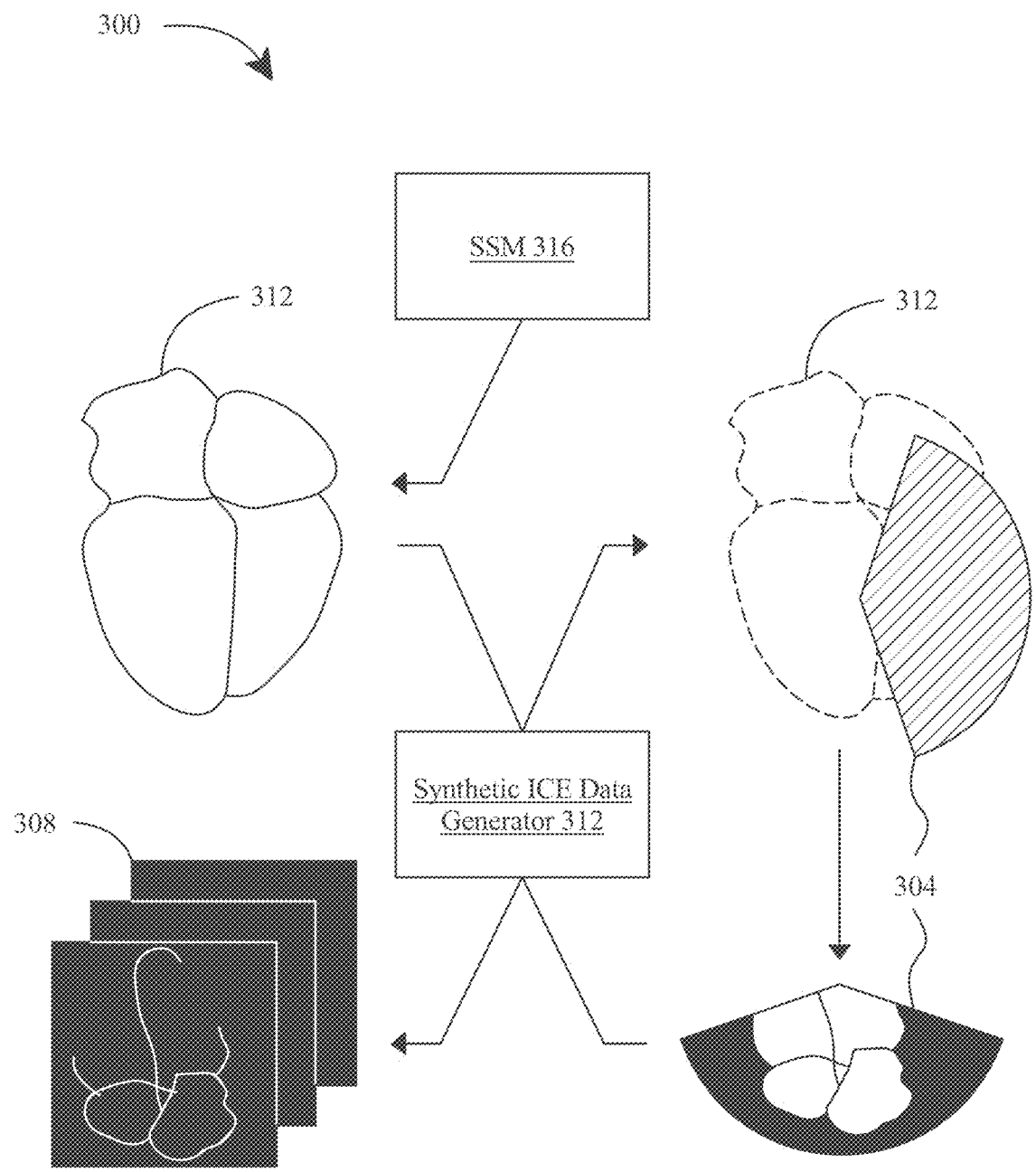
FIG. 3 is a flow diagram of an exemplary embodiment of an ICE image example generation process.

Now referring to FIG. 3, a flow diagram of an exemplary embodiment of an ICE example generation process 300. In an embodiment, cardiac anatomy training data may be generated, at least in part, via ICE example generation process 300. In some cases, processor 104 may be configured to receive a 3D model of the heart, such as any 3D model of cardiac anatomy 312 as described herein and identify an ICE view 304 (i.e., visual representation of image obtained using intracardiac echocardiography as described above e.g., ICE image 200) based on the received 3D model. In some cases, 3D model received by processor 104 may be derived from CT scans as described above with reference to FIG. 1. In other cases, processor may receive CT scans directly instead of 3D models. A synthetic ICE frame 308 may then be generated, by processor 104, as a function of identified ICE view 304, wherein the synthetic ICE frame 208 may be used as one or the training examples in cardiac anatomy training data.

With continued reference to FIG. 3, in some cases, processor 104 may interface with one or more 3D models (i.e., detailed representation of heart's anatomy in a 3D space, capturing intricate structures, chambers, vessels, valves, among others) as described above, or other imaging modalities and/or databases, and equipped with algorithms e.g., CNN, gradient boosting machines, SVM, PCA, and/or the like to analyze model's geometry and spatial relationships upon receiving the 3D models. In some cases, 3D models may be received from SSM 316 as described above with reference to FIG. 1 via a communicative connection between processor 104 and SSM 316. In a non-limiting example, processor 104 may be configured to determine an optimal viewpoints or angles from which ICE view 304 would provide a desired diagnostic value or procedural guidance.

Still referring to FIG. 3, in some cases, identification and selection of ICE view 304 may be automatically identified, using one or more machine learning models as described herein. In a non-limiting example, processor 104 may utilize one or more machine learning models trained on cardiac anatomy viewpoints identification training data, wherein the cardiac anatomy viewpoints identification training data may include a plurality of cardiac anatomies as input correlated to a plurality of ICE images as output and identify at least one ICE view 304 (most informative) for a given cardiac anatomy using the trained machine learning models.

Still referring to FIG. 3, in other cases, ICE view 304 may be defined by a user such as a medical professional. In a non-limiting example user interface of display device may allow a user (e.g., a clinician) to manually rotate, pan, and zoom displayed 3D model and/or corresponding CT scans. As user do so, processor 104 may dynamically calculate and displays potential ICE views 304 based on user's chosen perspective. Additionally, or alternatively, depending on cardiac procedure being planned or executed, processor 104 may prioritize certain ICE views 304. For instance, and without limitation, ICE view 304 may be pre-defined. For atrial fibrillation ablation, ICE view 304 may showcase the pulmonary veins' entrances into the LA may be emphasized. In other cases, ICE view 304 may be automatically identified, by processor 104, using one or more machine learning models as described herein, such as, without limitation, synthetic ICE data generator as described in detail below.

With continued reference to FIG. 3, as used in this disclosure, a "synthetic ICE frame" refers to a digitally generated or simulated image that emulates a visual representation obtained from ICE view 304. In some cases, synthetic ICE frames 308 may be produced using computational methods and/or models such as, without limitation, a synthetic ICE data generator based on pre-existing data, models, or simulations e.g., identified ICE views 304. In a non-limiting example, synthetic ICE frames 308 may include a simplified version e.g., an image illustrating heart anatomy via a plurality of lines indicating contours of heart's structure as shown in FIG. 3. One or more image processing techniques and/or computer vision algorithms such as, without limitation, histogram equalization, adaptive filtering, edge detection (e.g., Canny or Sobel operators), contour extraction, and/or the like may be applied, by processor 104, on a segmented CT scan and/or 3D models based on identified ICE view 304. Synthetic ICE frame 308 may be rendered on a blank canvas or background that mimics the echogenicity of an ICE image according to extracted contours, wherein the extracted contours may be represented as a bold lines and enhanced with shading to give depth. In some cases, synthetic ICE frame 308 may be validated and verified by overlaying synthetic ICE frame 308 onto original ICE view 304, ensuring accuracy and resemblance.

Still referring to FIG. 3, in some cases, generating synthetic ICE frames 308 may include implementations of one or more aspects of "generative artificial intelligence," a type of AI that uses machine learning algorithms to create, establish, or otherwise generate data such as, without limitation, ICE images, ICE videos, and/or the like that is similar to one or more provided training examples. In an embodiment, machine learning module described herein may generate one or more generative machine learning models that are trained on one or more set of CT scans and/or 3D models in ICE image view 304 as described above. Synthetic ICE data generator may include one or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 3, in some cases, generative machine learning models within synthetic ICE data generator may include one or more generative models. As described herein, "generative models" refers to statistical models of the joint probability distribution P(X, Y) on a given observable variable x, representing features or data that can be directly measured or observed (e.g. CT scans and/or 3D models derived from CT scans) and target variable y, representing the outcomes or labels that one or more generative models aims to predict or generate (e.g., synthetic ICE frames 308). In some cases, generative models may rely on Bayes theorem to find joint probability; for instance, and without limitation, Naïve Bayes classifiers may be employed by computing device to categorize input data such as, without limitation, CT scans and/or 3D models derived from CT scans into different views.

In a non-limiting example, and still referring to FIG. 3, one or more generative machine learning models may include one or more Naïve Bayes classifiers generated, by processor 104, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction.

Still referring to FIG. 3, although Naïve Bayes classifier may be primarily known as a probabilistic classification algorithm; however, it may also be considered a generative model described herein due to its capability of modeling the joint probability distribution $P(X, Y)$ over observable variables X and target variable Y. In an embodiment, Naïve Bayes classifier may be configured to make an assumption that the features X are conditionally independent given class label Y, allowing generative model to estimate the joint distribution as $P(X, Y)=P(Y)\Pi i P(Xi|Y)$, wherein $P(Y)$ may be the prior probability of the class, and $P(X_i|Y)$ is the conditional probability of each feature given the class. One or more generative machine learning models containing Naïve Bayes classifiers may be trained on labeled training data, estimating conditional probabilities $P(X_i|Y)$ and prior probabilities $P(Y)$ for each class; for instance, and without limitation, using techniques such as Maximum Likelihood Estimation (MLE). One or more generative machine learning models containing Naïve Bayes classifiers may select a class label y according to prior distribution $P(Y)$, and for each feature $X_i$, sample at least a value according to conditional distribution $P(X_i|y)$. Sampled feature values may then be combined to form one or more new data instance with selected class label y. In a non-limiting example, one or more generative machine learning models may include one or more Naïve Bayes classifiers to generate new examples of ICE images based on CT scans and/or 3D models derived from CT scans (e.g., identified ICE views 304), wherein the models may be trained using training data containing a plurality of features of input data as described herein and/or the like correlated to a plurality of ICE views.

Still referring to FIG. 3, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIGS. 5-7.

With continued reference to FIG. 3, in an embodiment, discriminator may include one or more discriminative models, i.e., models of conditional probability $P(Y|X=x)$ of target variable Y, given observed variable X. In an embodiment, discriminative models may learn boundaries between classes or labels in given training data. In a non-limiting example, discriminator may include one or more classifiers as described in further detail below with reference to FIG. 5 to distinguish between different categories e.g., real vs. fake, or states e.g., TRUE vs. FALSE within the context of generated data such as, without limitations, synthetic ICE frames 308, and/or the like. In some cases, processor 104 may implement one or more classification algorithms such as, without limitation, Support Vector Machines (SVM), Logistic Regression, Decision Trees, and/or the like to define decision boundaries.

In a non-limiting example, and still referring to FIG. 3, generator of GAN may be responsible for creating synthetic data that resembles real ICE images. In some cases, GAN may be configured to receive CT scans and/or 3D models derived from CT scans as input and generates corresponding examples of ICE images containing information describing heart anatomy in different ICE views. On the other hand, discriminator of GAN may evaluate the authenticity of the generated content by comparing it to true ICE images, for example, discriminator may distinguish between genuine and generated content and providing feedback to generator to improve the model performance. Additionally, or alternatively, GAN may include a conditional GAN as an extension of the basic GAN as described herein that allows for generation of ICE images using pre-existing CT scans and/or 3D models derived from CT scans based on certain conditions or labels. In standard GAN, generator may produce samples from random noise, while in a conditional GAN, generator may produce samples based on random noise and a given condition or label.

With continued reference to FIG. 3, in other embodiments, one or more generative models may also include a variational autoencoder (VAE). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from the latent space to the input space.

In a non-limiting example, and still referring to FIG. 3, VAE may be used by processor 104 to model complex relationships between CT scans and/or 3D models derived from CT scans. In some cases, VAE may encode input data into a latent space, capturing example ICE images. Such encoding process may include learning one or more probabilistic mappings from observed CT scans and/or 3D models derived from CT scans to a lower-dimensional latent representation. Latent representation may then be decoded back into the original data space, therefore reconstructing the 3D models representing example ICE images. In some cases, such decoding process may allow VAE to generate new examples or variations that are consistent with the learned distributions.

Additionally, or alternatively, and still referring to FIG. 3, processor 104 may be configured to continuously monitor synthetic ICE data generator. In an embodiment, processor 104 may configure discriminator to provide ongoing feedback and further corrections as needed to subsequent input data. An iterative feedback loop may be created as processor 104 continuously receive real-time data, identify errors (e.g., distance between synthetic ICE frame 308 and real ICE images) as a function of real-time data, delivering corrections based on the identified errors, and monitoring subsequent model outputs and/or user feedbacks on the delivered corrections. In an embodiment, processor 104 may be configured to retrain one or more generative machine learning models within synthetic ICE data generator based on user modified ICE frames or update training data of one or more generative machine learning models within synthetic ICE data generator by integrating validated synthetic ICE frames (i.e., subsequent model output) into the original training data. In such embodiment, iterative feedback loop may allow synthetic ICE data generator to adapt to the user's needs and performance requirements, enabling one or more generative machine learning models described herein to learn and update based on user responses and generated feedbacks.

With continued reference to FIG. 3, other exemplary embodiments of generative machine learning models may include, without limitation, long short-term memory networks (LSTMs), (generative pre-trained) transformer (GPT) models, mixture density networks (MDN), and/or the like. As an ordinary person skilled in the art, upon reviewing the entirety of this disclosure, will be aware of various generative machine learning models that may be used generating synthetic ICE frames 308.

Still referring to FIG. 3, in a further non-limiting embodiment, synthetic ICE data generator may be further configured to generate a multi-model neural network that combines various neural network architectures described herein. In a non-limiting example, multi-model neural network may combine LSTM for time-series analysis with GPT models for natural language processing. Such fusion may be applied by computing device to generate synthetic ICE frames 308. In some cases, multi-model neural network may also include a hierarchical multi-model neural network, wherein the hierarchical multi-model neural network may involve a plurality of layers of integration; for instance, and without limitation, different models may be combined at various stages of the network. Convolutional neural network (CNN) may be used for image feature extraction, followed by LSTMs for sequential pattern recognition, and a MDN at the end for probabilistic modeling. Other exemplary embodiments of multi-model neural network may include, without limitation, ensemble-based multi-model neural network, cross-modal fusion, adaptive multi-model network, among others. As an ordinary person skilled in the art, upon reviewing the entirety of this disclosure, will be aware of various generative machine learning models that may be used to generating synthetic ICE frames 308 as described herein. As an ordinary person skilled in the art, upon reviewing the entirety of this disclosure, will be aware of various multi-model neural network and combination thereof that may be implemented in consistent with this disclosure.

Figure 4:
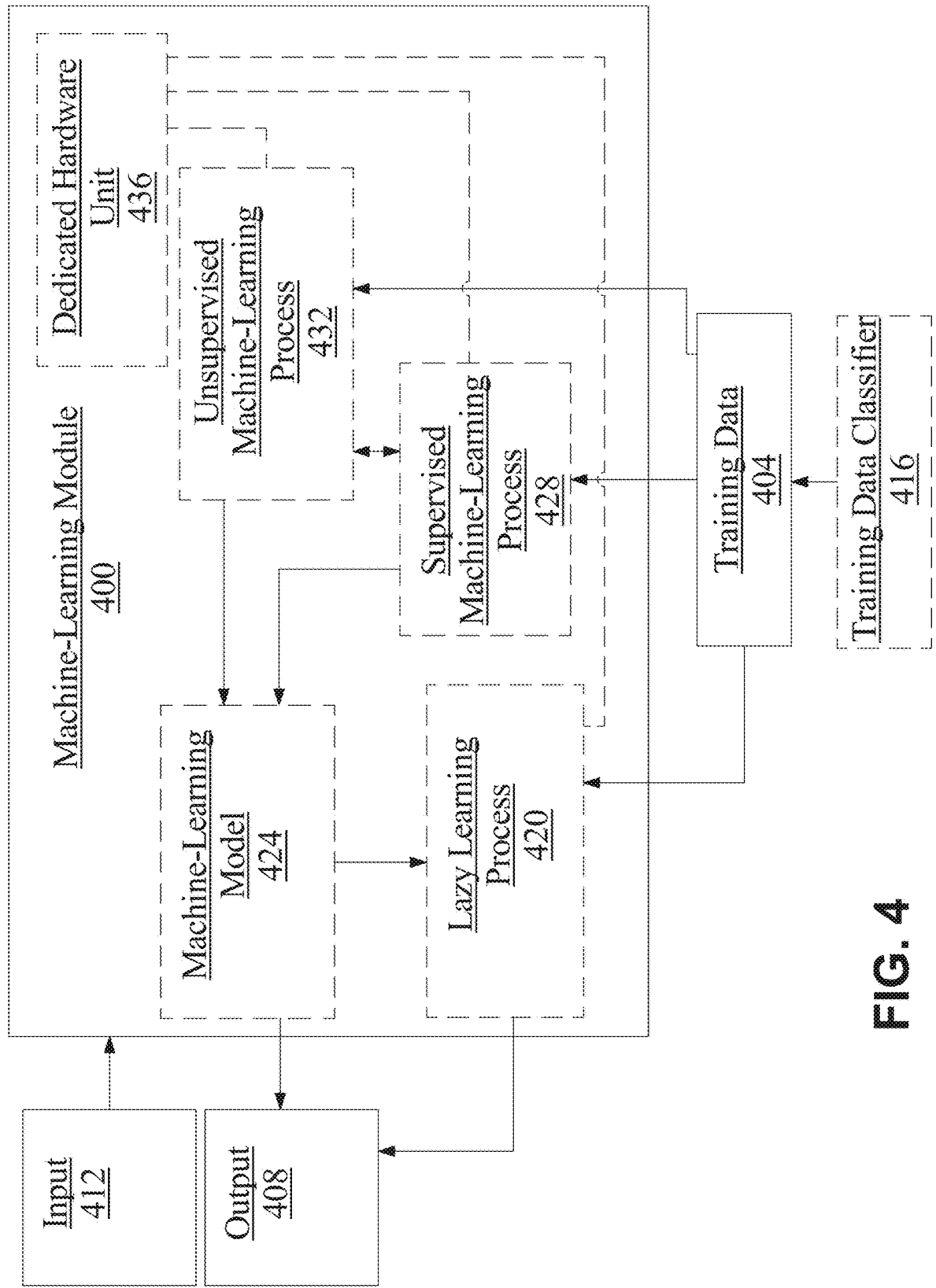
FIG. 4 is a block diagram of an exemplary embodiment of a machine learning model.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm instantiated in hardware or software logic, data structures, and/or functions that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example, inputs may include user inputs and outputs may include an agent selection datum.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to particular medical procedures.

Still referring to FIG. 4, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 4, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 4, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 4, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 4, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 4, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 4, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 4, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 4, computing device, processor, and/or module may down-sample elements of a training example to a desired lower number of data elements. As a non-limiting example, a high pixel count image may have 256 pixels, however a desired number of pixels may be 128. Processor may downsample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Antialiasing and/or anti-imaging filters, and/or low-pass filters, may be used to clean up side-effects of compression.

Further referring to FIG. 4, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max} : X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation a of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 4, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include user inputs as described above as inputs, agent selection data as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

With further reference to FIG. 4, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 4, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 432 may not require a response variable; unsupervised processes 432 may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 4, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 4, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 4, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 4, one or more processes or algorithms described above may be performed by at least a dedicated hardware unit 436. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 436 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 436 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 436 to perform one or more operations described herein, such as evaluation of model and/or algorithm outputs, one-time or iterative updates to parameters, coefficients, weights, and/or biases, and/or any other operations such as vector and/or matrix operations as described in this disclosure.

With continued reference to FIG. 4, system 100 may use user feedback to train the machine-learning models and/or classifiers described above. For example, classifier may be trained using past inputs and outputs of classifier. In some embodiments, if user feedback indicates that an output of classifier was "bad," then that output and the corresponding input may be removed from training data used to train classifier, and/or may be replaced with a value entered by, e.g., another user that represents an ideal output given the input the classifier originally received, permitting use in retraining, and adding to training data; in either case, classifier may be retrained with modified training data as described in further detail below. In some embodiments, training data of classifier may include user feedback.

With continued reference to FIG. 4, in some embodiments, an accuracy score may be calculated for classifier using user feedback. For the purposes of this disclosure, "accuracy score," is a numerical value concerning the accuracy of a machine-learning model. For example, a plurality of user feedback scores may be averaged to determine an accuracy score. In some embodiments, a cohort accuracy score may be determined for particular cohorts of persons. For example, user feedback for users belonging to a particular cohort of persons may be averaged together to determine the cohort accuracy score for that particular cohort of persons and used as described above. Accuracy score or another score as described above may indicate a degree of retraining needed for a machine-learning model such as a classifier; system 100 may perform a larger number of retraining cycles for a higher number (or lower number, depending on a numerical interpretation used), and/or may collect more training data for such retraining, perform more training cycles, apply a more stringent convergence test such as a test requiring a lower mean squared error, and/or indicate to a user and/or operator that additional training data is needed.

Figure 5:
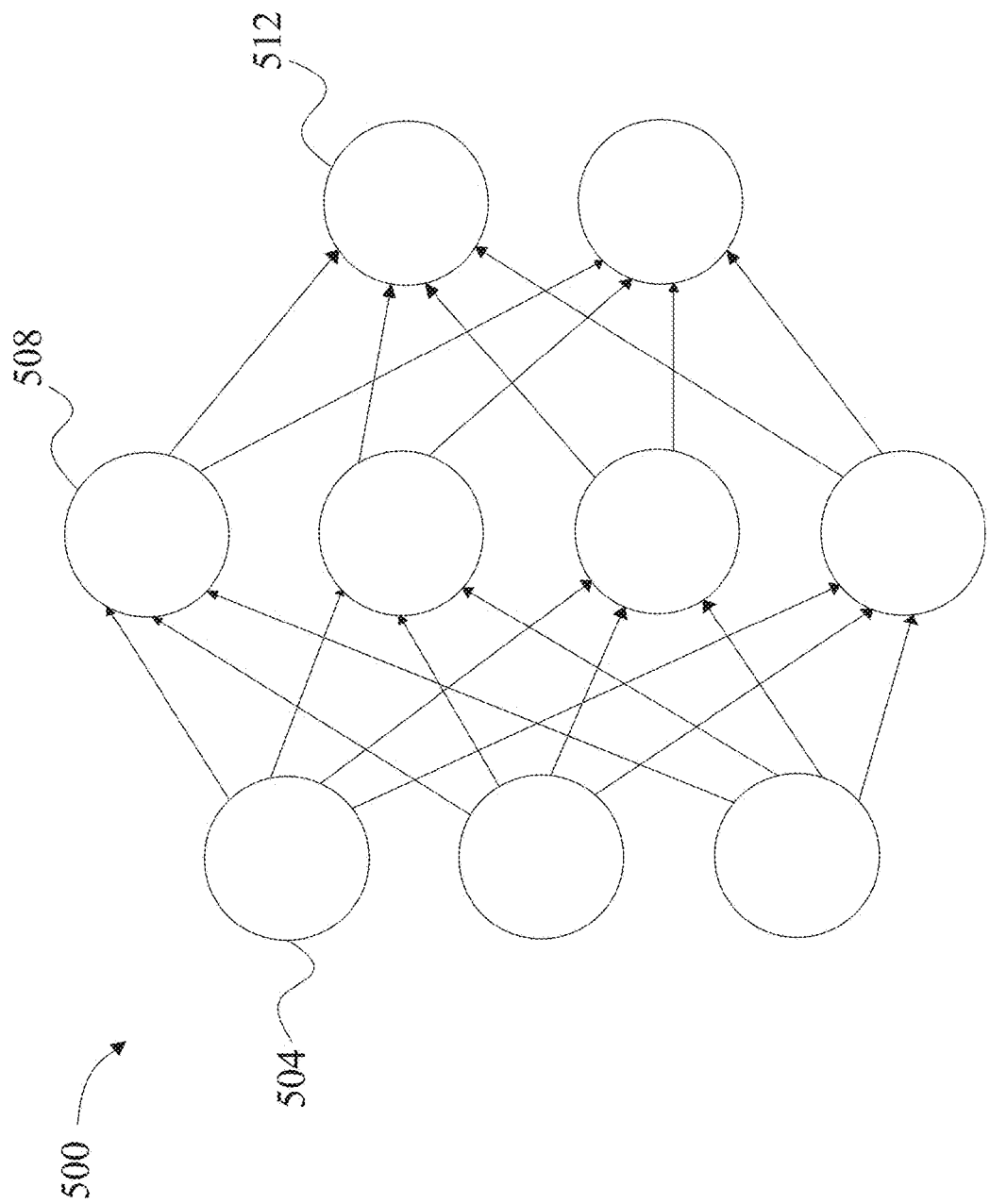
FIG. 5 is a schematic diagram of an exemplary embodiment of a neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes.

Figure 6:
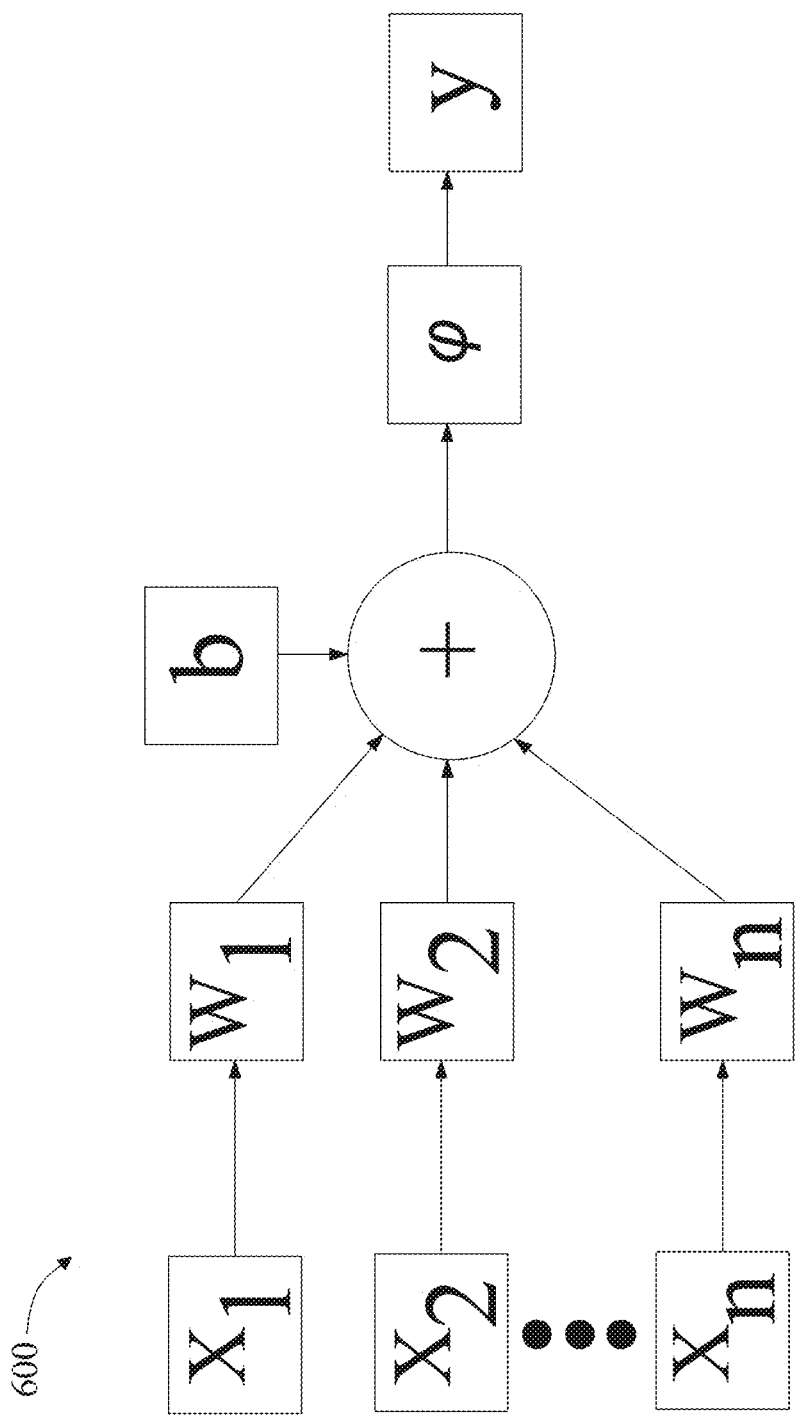
FIG. 6 is a schematic diagram of an exemplary embodiment of a neural network node.

Referring now to FIG. 6, an exemplary embodiment of a node 600 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tan h (hyperbolic tangent) function, of the form $$\frac{e^x - e^{-x}}{e^x + e^{-x}},$$

a tan h derivative function such as $f(x)=\tan h^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tan h(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 6, a "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like. CNN may include, without limitation, a deep neural network (DNN) extension, where a DNN is defined as a neural network with two or more hidden layers.

Figure 7:
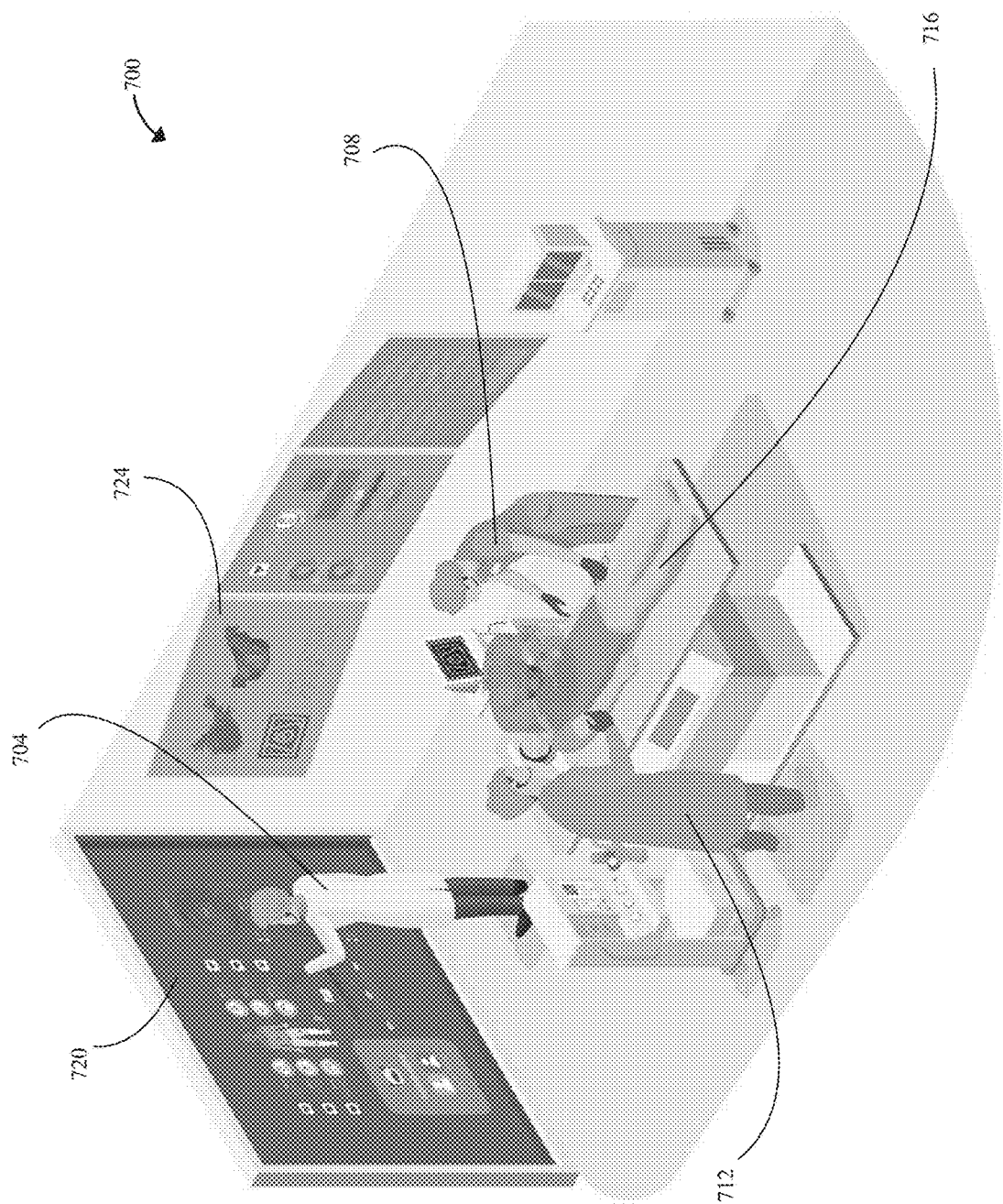
FIG. 7 is an illustration of an exemplary operatory during an electrophysiology procedure using an exemplary stylized electrophysiology copilot.

Referring now to FIG. 7, a representation of an exemplary operatory 700 during an electrophysiology procedure using an exemplary stylized electrophysiology copilot is shown. In some embodiments, operatory 700 may include one or more users such as users 704, 708, and 712, which may operate a system such as an electrophysiology copilot described herein. Operatory 700 may further include subject 716. Operatory 700 may further include one or more interfaces, such as interfaces 720 and 724. Such interfaces may, in non-limiting examples, display procedure data as described herein and/or allow users to input data into electrophysiology copilot. In some embodiments, an electrophysiology copilot may be consistent with a system described above, such as a system including an agent orchestrator and one or more agents. An electrophysiology copilot may include an agentic artificial intelligence (AI) system that implements a co-pilot for operators, physicians, mappers and/or technicians involved in an electrophysiology procedure (EP). In some embodiments, tasks commonly performed today by technicians and mappers, for instance at voice instruction by a physician, may be performed by an agentic AI system. An agentic AI system may provide specific functionality such as, in non-limiting examples, patient specific information retrieval germane to EP procedure, either as an unprompted recommendation or based on a voice, text, or touch-based command. In some cases, a user, via an agentic AI system may pose clinical queries and/or hypotheses to a real world database, including, for example, a database of details of prior EP procedures. In some embodiments, an agentic AI system may, again as an unprompted recommendation or based on a user command, present specific views to physician. Agentic AI may, without limitation, make specific recommendations that are clinical, to be considered intra-operatively, based on patient, cohort, and/or context. Agentic AI may recommend a specific motion along specific paths for any of a number of catheters. In some embodiments, agentic AI may be in communication (e.g., real-time communication) with (1) devices configured for ambient sensing of events; (2) sensors attached to catheters; and/or (3) other medical devices. In some cases, based upon external and/or internal signals, agentic AI may trigger notifications, alarms, or other specific actions, including but not restricted to (1) automatically displaying specific imaging views, angles, or perspectives, with or without appropriate voiceovers, as required; and (2) autonomous control sequence of one or more specific EP devices, e.g. catheters.

Figure 8:
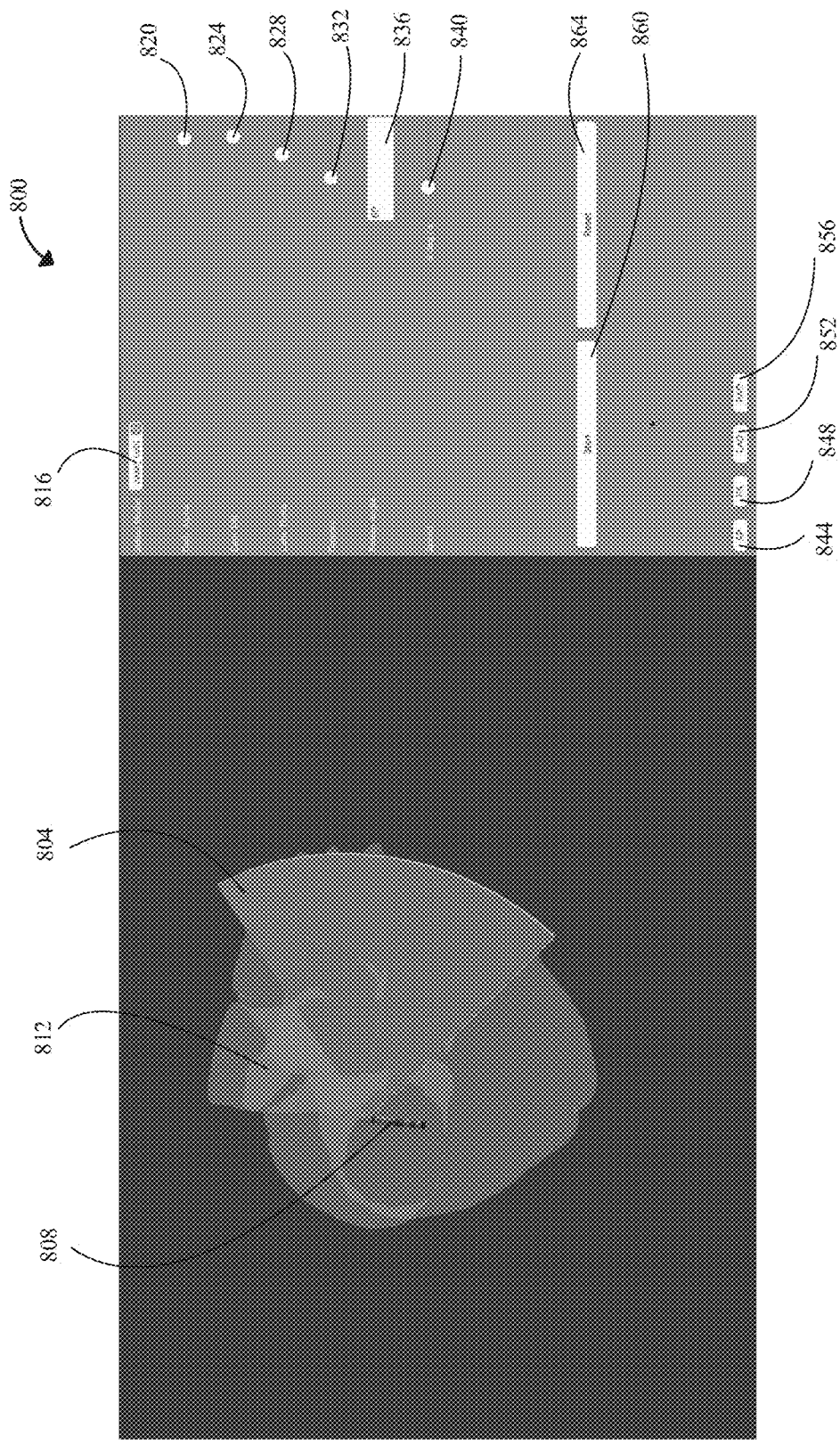
FIG. 8 is an illustration of an exemplary embodiment of an interface of an electrophysiology copilot.

Referring now to FIG. 8, an illustration of an exemplary interface 800 for an electrophysiology copilot is provided. In some embodiments, electrophysiology copilot may depict a position of a catheter within an organ such as a heart. In some embodiments, electrophysiology copilot may depict a field of view 804 of a sensor of a catheter 808, e.g. an intracardiac echocardiogram (ICE) or transesophageal echocardiogram (TEE) ultrasonic transducer, with respect to a modeled organ 812. In some embodiments, electrophysiology copilot may include functionality for selecting one or more models, such as through use of interactable element 816. In some embodiments, electrophysiology copilot may include one or more settings for viewing a model, such as Catheter Alpha 820, Catheter Phi 824, and/or Catheter Theta 828, which may control an orientation of a catheter. In some embodiments, interface 800 may further include an opacity setting 832, which may control an opacity of modelled organ 816. In some embodiments, electrophysiology copilot may be used to view a field of view as it sweeps around a catheter. Non-limiting examples of settings which may be adjusted for viewing a moving field of view include sweep angle 836 and speed 840. In some embodiments, a depicted field of view may include a 2D slice or cross-section of a 3D model. In some embodiments, interface 800 may further include one or more interactable elements, such as interactable elements 844, 848, 852, and 856, which position and/or orient a perspective to a predetermined position with respect to a modelled organ, such as a left anterior oblique (LAO) view, a right anterior oblique (RAO), an anteroposterior (AP), or a posteroanterior (PA) position. Interface 800 may further include an interactable element 860 which starts movement of a field of view with respect to a 3D model, and/or an interactable element 864 which resets a field of view with respect to a 3D model.

Still referring to FIG. 8, electrophysiology copilot may generate 3D mesh from ICE-based 3D or a cardiac computed tomography (CT). In some embodiments, a user such as a physician or technician may use electrophysiology copilot to do one or more of the following actions, one or more times: (a) Specify using an input such as a mouse, touch, voice, keyboard, text, or other input a trajectory to be followed by an ICE catheter to create a sequence of "ICE views." Such ICE views may include, or be used to derive, metrics such as frame rates, angles between each frame, overall sweep angle, and the like. In some embodiments, ICE views may have corresponding "synthetic ICE frames" which may be used for downstream training of an ICE to 3d system. (b) Train junior physicians or technicians on what trajectories are to be taken by the ICE catheter to capture good views of specific structures in specific chambers. Or (c) train junior physicians or technicians on what trajectories are to be taken by the ICE catheter to capture good views of specific structures in specific chambers, in response to an ICE video the junior physician has been shown and asked to reproduce. In some embodiments, an electrophysiology copilot may be used for similar training with other catheter types. In some embodiments, an electrophysiology copilot may be operated through use of voice based commands. In a non-limiting example, a system may respond to a user voice command such as: "show me the view if a camera were to be placed on the coronary sinus, facing towards the left atrial appendage (LAA)."

Figure 9:
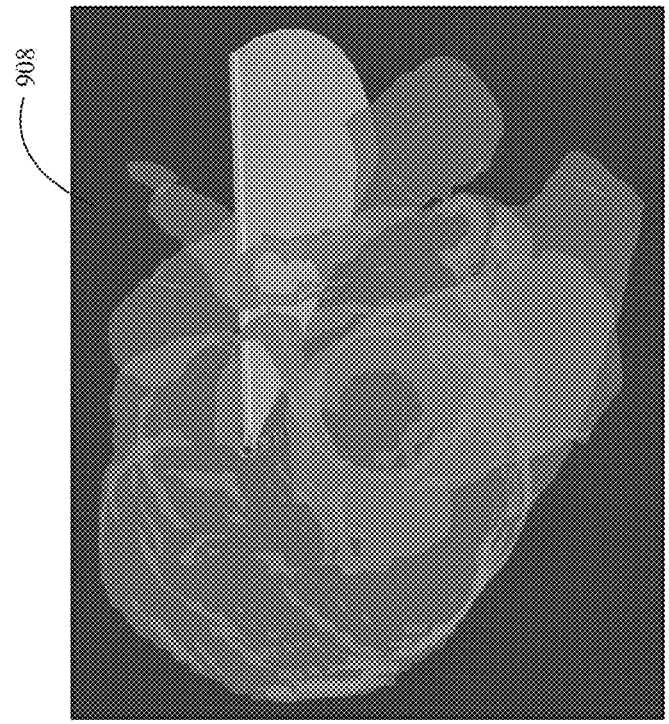
FIG. 9 includes 2 illustrations of exemplary embodiments of an interface of an electrophysiology copilot.
Figure 9:
Figure 9:
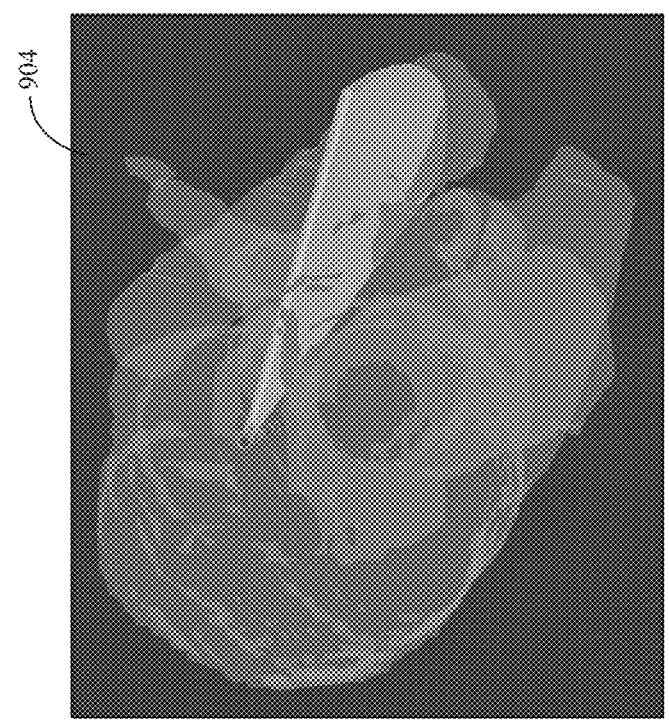

Referring now to FIG. 9, two illustrations of exemplary embodiments of an interface of an electrophysiology copilot are provided, while a catheter sensor is swept within a heart. In some embodiments, an interface may depict a field of view of a sensor on a catheter rotating around a catheter. For example, a catheter may remain translationally stationary (aside from rotating) and a field of view may rotate (i.e., sweep) from a position depicted in image 904 to a position depicted in image 908. In some embodiments, a sensor depicted using an electrophysiology copilot interface may include, in non-limiting examples, an ICE or TEE ultrasound transducer. In some embodiments, a field of view sweep may be performed for 3D model construction and/or catheter localization.

Figure 10:
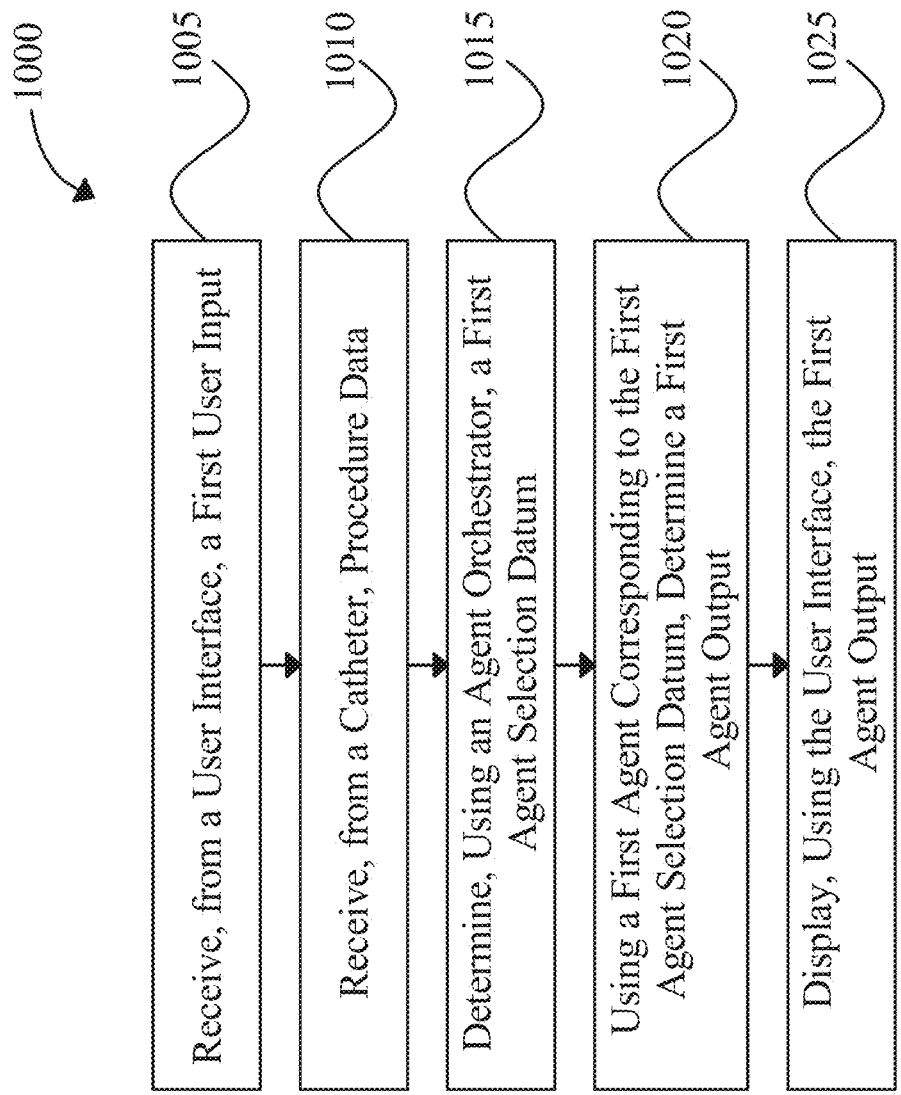
FIG. 10 is a flow diagram depicting an exemplary embodiment of a method of responding to a user input using an agent orchestrator.

Referring now to FIG. 10, an exemplary embodiment of a method 1000 of responding to a user input using an agent orchestrator is illustrated. One or more steps if method 1000 may be implemented, without limitation, as described with reference to other figures. One or more steps of method 1000 may be implemented, without limitation, using at least a processor.

Still referring to FIG. 10, in some embodiments, method 1000 may include a step 1005 of receiving, from a user interface, a first user input.

Still referring to FIG. 10, in some embodiments, method 1000 may include a step 1010 of receiving, from a catheter, procedure data. In some embodiments, the procedure data includes catheter location data.

Still referring to FIG. 10, in some embodiments, method 1000 may include a step 1015 of using an agent orchestrator, determining a first agent selection datum. In some embodiments, step 1015 may include generating the first agent selection datum as a function of the first user input using a trained agent selection machine learning model.

Still referring to FIG. 10, in some embodiments, method 1000 may include a step 1020 of using a first agent corresponding to the first agent selection datum, determining a first agent output. In some embodiments, step 1020 may include inputting into the first agent the procedure data and receiving, as an output from the first agent, the first agent output. In some embodiments, the procedure data includes ultrasonic image data. In some embodiments, the first agent is configured to generate a set of shape parameters representing a structure's shape as a function of the ultrasonic image data and a shape identification model trained on a training dataset includes historical ultrasonic images correlated with historical computed tomography scan data and generate a 3D model of the structure based on the set of shape parameters, wherein the first agent output includes the 3D model. In some embodiments, the procedure data includes a Pulsed Field Ablation (PFA) device parameter and determining the first agent output includes generating a PFA durability datum as a function of the PFA device parameter using a trained PFA durability machine learning model. In some embodiments, the procedure data includes a Pulsed Field Ablation (PFA) device parameter, and the first agent includes a lesion durability agent configured to generate a PFA durability datum as a function of the PFA device parameter using a trained PFA durability machine learning model; and the first agent output includes the PFA durability datum.

Still referring to FIG. 10, in some embodiments, method 1000 may include a step 1025 of, using the user interface, displaying the first agent output. In some embodiments, the first user input includes audio input data, and displaying the first agent output includes converting the first agent output to audio output data and outputting the audio output data.

Still referring to FIG. 10, in some embodiments, method 1000 further includes generating an encoded user input as a function of the first user input using a first trained language model, and generating the first agent selection datum as a function of the first user input includes inputting into a trained agent selection machine learning model the encoded user input, and receiving, as an output from the trained agent selection machine learning model, the first agent selection datum.

Still referring to FIG. 10, in some embodiments, method 1000 further includes generating, using a second language model, a natural language response based on the first agent output, and displaying the first agent output includes displaying the natural language response.

Still referring to FIG. 10, in some embodiments, method 1000 further includes receiving, from the user interface, a second user input, retrieving, from an electronic health record database, electronic health record data, determining, using the agent orchestrator, a second agent selection datum by generating the second agent selection datum as a function of the second user input using the trained agent selection machine learning model, using a second agent corresponding to the second agent selection datum, determining a second agent output by inputting into the second agent at least a portion of the electronic health record data, and receiving, as an output from the second agent, the second agent output, and displaying, using the user interface, the second agent output.

Still referring to FIG. 10, in some embodiments, method 1000 further includes receiving, from the user interface, a third user input, receiving an electrocardiogram (ECG) datum, determining, using the agent orchestrator, a third agent selection datum by generating the third agent selection datum as a function of the third user input using the trained agent selection machine learning model, using a third agent corresponding to the third agent selection datum, determining a third agent output by inputting into the third agent the ECG datum, and receiving, as an output from the third agent, a signal metric, and displaying, using the user interface, the signal metric. In some embodiments, method 1000 may further include receiving, from an electrocardiogram (ECG) sensor, an ECG datum, determining, using the agent orchestrator, a second agent selection datum by generating the second agent selection datum as a function of the ECG datum, using a second agent corresponding to the third agent selection datum, determine a second agent output by inputting into the third agent the ECG datum, receiving, as an output from the second agent, an abnormality datum, and display, using the user interface, the abnormality datum.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
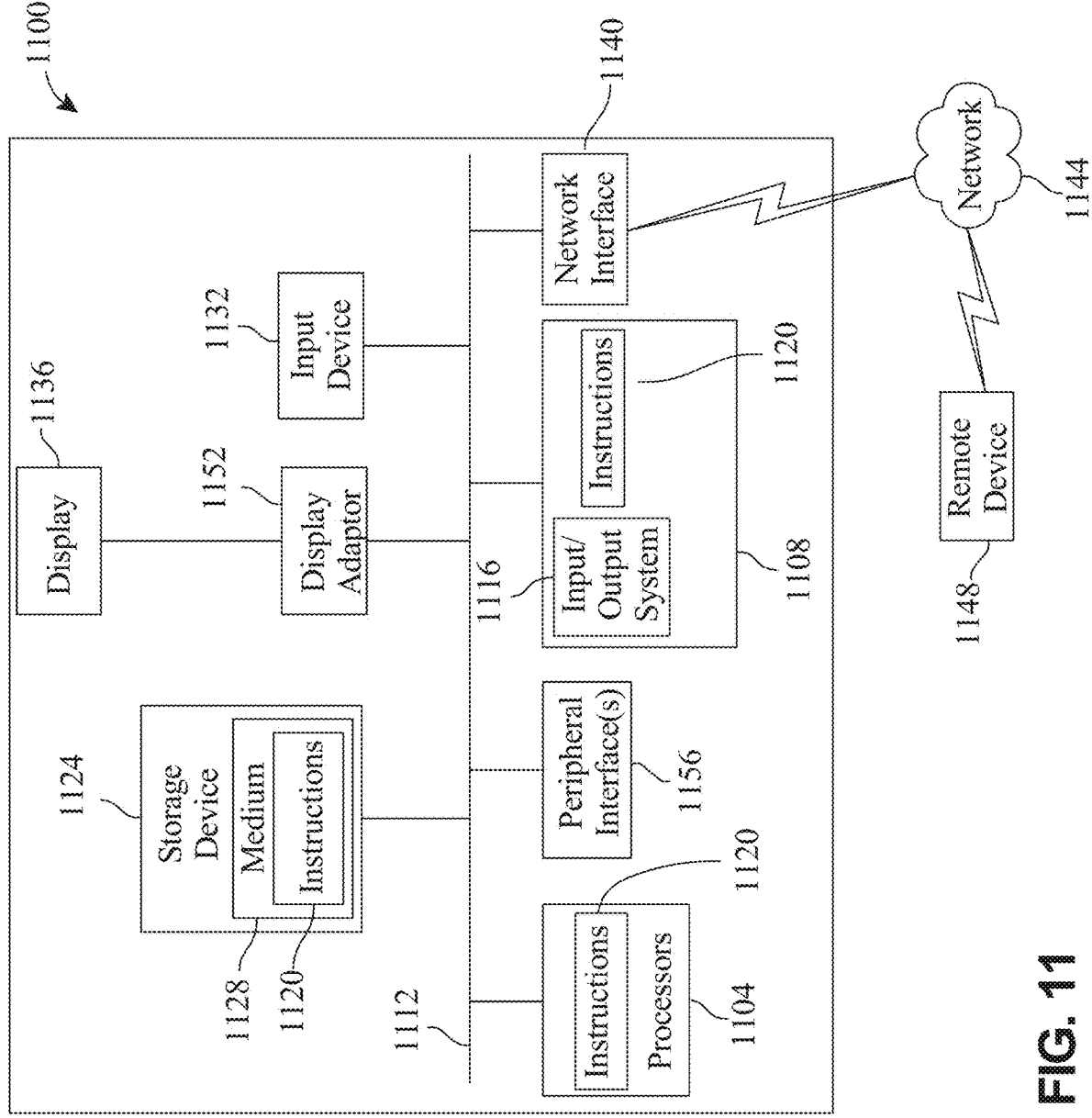
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Processor 1104 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1104 may be organized according to Von Neumann and/or Harvard architecture as a non-limiting example. Processor 1104 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display device 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for responding to a user input using an agent orchestrator, the system comprising:

a catheter, wherein the catheter is configured to detect procedure data;
a user interface; at least a processor; and a memory communicatively connected to the at least a processor, wherein the memory contains instructions configuring the at least a processor to:
receive, from the user interface, a first user input;
receive, from the catheter, the procedure data that includes ultrasonic image data;
determine, using an agent orchestrator, a first agent selection datum,
generating the first agent selection datum as a function of the first user input using a trained agent selection machine learning model;
generating a set of shape parameters representing a structure's shape as a function of the ultrasonic image data and a shape identification model trained on a training dataset comprising historical ultrasonic images correlated with historical computed tomography scan data;
generating a 3D model of the structure based on the set of shape parameters,
using a first agent corresponding to the first agent selection datum, determine a first agent output, by inputting into the first agent the procedure data; and receiving, as an output from the first agent, the first agent output including the 3D model; and display, using the user interface, the first agent output.

2. The system of claim 1, wherein: the first user input comprises audio input data; and displaying the first agent output by converting the first agent output to audio output data and outputting the audio output data.

3. The system of claim 1, wherein the memory contains instructions configuring the at least a processor to:
generate an encoded user input as a function of the first user input using a first trained language model;
and generating the first agent selection datum as a function of the first user input by inputting, into a trained agent selection machine learning model, the encoded user input; and receiving, as an output from the trained agent selection machine learning model, the first agent selection datum.

4. The system of claim 1, wherein the memory contains instructions configuring the at least a processor to:
generate, using a second language model, a natural language response based on the first agent output; and displaying the first agent output by displaying the natural language response.

5. The system of claim 1, wherein the memory contains instructions configuring the at least a processor to:
receive, from the user interface, a second user input;
retrieve, from an electronic health record database, electronic health record data;
determine, using the agent orchestrator, a second agent selection datum;
generating the second agent selection datum as a function of the second user input using the trained agent selection machine learning model; using a second agent corresponding to the second agent selection datum, determine a second agent output by inputting into the second agent at least a portion of the electronic health record data; and receiving, as an output from the second agent, the second agent output; and display, using the user interface, the second agent output.

6. The system of claim 1, wherein the procedure data comprises: a Pulsed Field Ablation (PFA) device parameter; the first agent comprises a lesion durability agent configured to generate a PFA durability datum as a function of the PFA device parameter using a trained PFA durability machine learning model; and the first agent output comprises the PFA durability datum.

7. The system of claim 1, wherein the memory contains instructions configuring the at least a processor to:
receive, from an electrocardiogram (ECG) sensor, an ECG datum;
determine, using the agent orchestrator, a second agent selection datum by H generating the second agent selection datum as a function of the ECG datum; using a second agent corresponding to a third agent selection datum, determine a second agent output by inputting into the third agent the ECG datum; receiving, as an output from the second agent, an abnormality datum; and display, using the user interface, the abnormality datum.

8. The system of claim 1, wherein the memory contains instructions configuring the at least a processor to:
receive, from the user interface, a second user input;
receive an electrocardiogram (ECG) datum; determine, using the agent orchestrator, a second agent selection datum by generating the second agent selection datum as a function of the second user input using the trained agent selection machine learning model; using a second agent corresponding to a third agent selection datum, determine a second agent output by: inputting into the third agent the ECG datum; and receiving, as an output from the second agent, a signal metric; and display, using the user interface, the signal metric.

9. A method of responding to a user input using an agent orchestrator, the method comprising: using at least a processor, receiving, from a user interface, a first user input; using the at least a processor, receiving, from a catheter, that includes ultrasonic image data;
using the at least a processor and an agent orchestrator, determining a first agent selection datum,
generating the first agent selection datum as a function of the first user input using a trained agent selection machine learning model;
generating a set of shape parameters representing a structure's shape as a function of the ultrasonic image data and a shape identification model trained on a training dataset comprising historical ultrasonic images correlated with historical computed tomography scan data; and generate a 3D model of the structure based on the set of shape parameters,
using the at least a processor and a first agent corresponding to the first agent selection datum, determining a first agent output, by inputting into the first agent the procedure data; and receiving, as an output from the first agent, the first agent output including the 3D model; and using the at least a processor and the user interface, displaying the first agent output.

10. The method of claim 9, wherein: the first user input comprises audio input data; and displaying the first agent output by converting the first agent output to audio output data and outputting the audio output data.

11. The method of claim 9, wherein the method further comprises;
generating an encoded user input as a function of the first user input using a first trained language model;
generating the first agent selection datum as a function of the first user input;
by inputting into a trained agent selection machine learning model the encoded user input; and receiving, as an output from the trained agent selection machine learning model, the first agent selection datum.

12. The method of claim 9, wherein the method further comprises: generating, using a second language model, a natural language response based on the first agent output; and displaying the first agent output comprises displaying the natural language response.

13. The method of claim 9, wherein the method further comprises: receiving, from the user interface, a second user input; retrieving, from an electronic health record database, electronic health record data; determining, using the agent orchestrator, a second agent selection datum by: generating the second agent selection datum as a function of the second user input using the trained agent selection machine learning model; using a second agent corresponding to the second agent selection datum, determining a second agent output by inputting into the second agent at least a portion of the electronic health record data; and receiving, as an output from the second agent, the second agent output; and displaying, using the user interface, the second agent output.

14. The method of claim 9, wherein the procedure data comprises: a Pulsed Field Ablation (PFA) device parameter; the first agent comprises a lesion durability agent configured to generate a PFA durability datum as a function of the PFA device parameter using a trained PFA durability machine learning model; and the first agent output comprises the PFA durability datum.

15. The method of claim 9, wherein the method further comprises: receiving, from an electrocardiogram (ECG) sensor, an electrocardiogram (ECG) datum; determining, using the agent orchestrator, a second agent selection datum by: generating the second agent selection datum as a function of the ECG datum; using a second agent corresponding to the second agent selection datum, determining a second agent output by inputting into the second agent the ECG datum; and receiving, as an output from the second agent, an abnormality datum; and displaying, using the user interface, the abnormality datum.

16. The method of claim 9, wherein the method further comprises: receiving, from the user interface, a second user input; receiving an electrocardiogram (ECG) datum; determining, using the agent orchestrator, a second agent selection datum by generating the second agent selection datum as a function of the second user input using the trained agent selection machine learning model; using a second agent corresponding to the second agent selection datum, determining a second agent output by inputting into the second agent the ECG datum; and receiving, as an output from the second agent, a signal metric; and displaying, using the user interface, the signal metric.

\* \* \* \* \*